(12) United States Patent
Bang et al.

(10) Patent No.: US 11,351,119 B2
(45) Date of Patent: Jun. 7, 2022

(54) STEM CELL-DERIVED MICROVESICLES WITH ENHANCED EFFICACY, USE THEREOF, AND METHOD FOR ENHANCING EFFICACY

(71) Applicants: SAMSUNG LIFE PUBLIC WELFARE FOUNDATION, Seoul (KR); RESEARCH & BUSINESS FOUNDATION SUNGKYUNKWAN UNIVERSITY, Gyeonggi-do (KR)

(72) Inventors: Oh Young Bang, Seoul (KR); Eun Hee Kim, Seoul (KR); Jae Min Cha, Seoul (KR)

(73) Assignees: SAMSUNG LIFE PUBLIC WELFARE FOUNDATION, Seoul (KR); RESEARCH & BUSINESS FOUNDATION SUNGKYUNKWAN UNIVERSITY, Gyeonggi-do (KR)

( * ) Notice: Subject to any disclaimer, the term of this patent is extended or adjusted under 35 U.S.C. 154(b) by 70 days.

(21) Appl. No.: 16/600,919

(22) Filed: Oct. 14, 2019

(65) Prior Publication Data
US 2020/0129433 A1 Apr. 30, 2020

(30) Foreign Application Priority Data

Oct. 25, 2018 (KR) .................. 10-2018-0128334
Oct. 14, 2019 (KR) .................. 10-2019-0127212

(51) Int. Cl.
*A61K 9/127* (2006.01)
*C12N 5/0735* (2010.01)
(Continued)

(52) U.S. Cl.
CPC ........ *A61K 9/1271* (2013.01); *A61K 31/7105* (2013.01); *C12N 5/0606* (2013.01); *C12N 5/0607* (2013.01); *C12N 2513/00* (2013.01)

(58) Field of Classification Search
CPC .. A61K 35/28; A61K 9/1271; C12N 2510/02; C12N 2513/00; C12N 5/0662;
(Continued)

(56) References Cited

FOREIGN PATENT DOCUMENTS

KR  10-2013-0019356 A   2/2013
KR  10-2015-0004822 A   1/2015
(Continued)

OTHER PUBLICATIONS

Hong et al. (Tissue Eng Regen Med., 2015 vol. 12:211-221).*
(Continued)

*Primary Examiner* — Terra C Gibbs
(74) *Attorney, Agent, or Firm* — Harness, Dickey & Pierce, P.L.C.

(57) ABSTRACT

The present invention relates to stem cell-derived microvesicles with enhanced efficacy, a use thereof, and a method for enhancing efficacy, and more particularly, to a use of stem cell-derived microvesicles with an enhanced expression level of microRNAs for the prevention or treatment of stroke, and a method for promoting the production of microRNAs of stem cell-derived microvesicles and enhancing efficacy, and a method for promoting the production of stem cell-derived microvesicles and microRNAs within the microvesicles and enhancing the efficacy of stem cells and microvesicles thereof by 3-dimensionally culturing or ischemically stimulating stem cells. Since the method according to the present invention has excellent effects capable of promoting the production of stem cell-derived microvesicles and microRNAs in the microvesicles and capable of enhancing the efficacy of stem cells or microvesicles isolated therefrom, it is possible to obtain stem cell-derived microvesicles containing high levels of materials including therapeutic microRNAs efficiently and in large quantities through this, and thus, the microvesicles are expected to be able to (Continued)

be usefully used in related research fields and future clinical settings.

11 Claims, 28 Drawing Sheets

(51) Int. Cl.
*A61K 31/7105* (2006.01)
*C12N 5/074* (2010.01)

(58) Field of Classification Search
CPC .. C12N 5/0663; C12N 5/0606; C12N 5/0607; C12N 5/0623
See application file for complete search history.

(56) References Cited

FOREIGN PATENT DOCUMENTS

| | | | |
|---|---|---|---|
| KR | 10-2017-0123852 A | 11/2017 | |
| KR | 10-2018-0111674 A | 10/2018 | |

OTHER PUBLICATIONS

Jarmalaviciute et al. (Cytotherapy, 2015 vol. 17:932-939).*
Saleh et al. (Progenitor Cells: Methods and Protocols, Methods in Molecular Biology, 2012 vol. 916:pp. 31-45).*
Azoidis et al. (MRS Communications, 2017 vol. 7:458-465).*
Egger et al. (Bioengineering, 2018 vol. 48:1-15).*
Moon, G. J., et al.; "Application of Mesenchymal Stem Cell-Derived Extracellular Vesicles for Stroke: Biodistribution and MicroRNA Study", Translational Stroke Research (2019) 10:509-521.
Lee, J. Y., et al.; "Microvesicles from brain-extract-treated mesenchymal stem cells improve neurological functions in a rat model of ischemic stroke", Sci. Rep. 6, 33038; doi: 10.1038/srep33038 (2016).
Jae Min Cha et al., "Efficient scalable production of therapeutic microvesicles derived from human mesenchymal stem cells" Scientific Reports, (2018) 8:1171 (Published on Jan. 19, 2018).
Biancone, L., et al.; "Therapeutic potential of mesenchymal stem cell-derived microvesicles", Nephrol. Dial. Transplant. 27, 3037-3042 (2012).

* cited by examiner

| | protein (μg/10⁵ cells) | p < 0.01 |
|---|---|---|
| 2D | 0.64 ± 0.07 | - |
| 2D w/shaking | 1.37 ± 0.17 | - |
| 3D | 1.90 ± 0.73 | - |
| 3D w/shaking | 10.66 ± 1.90 | ** |

FIG. 4C

STEM CELL-DERIVED MICROVESICLES WITH ENHANCED EFFICACY, USE THEREOF, AND METHOD FOR ENHANCING EFFICACY

CROSS-REFERENCE TO RELATED APPLICATION

This application claims priority to and the benefit of Korean Patent Application No. 2018-0128334, filed on Oct. 25, 2018 and No. 2019-0127212, filed on Oct. 14, 2019, the disclosure of which is incorporated herein by reference in its entirety.

FIELD

The present invention relates to stem cell-derived microvesicles with enhanced efficacy, a use thereof, and a method for enhancing efficacy, and more particularly, to a use of stem cell-derived microvesicles with an enhanced expression level of microRNAs for the prevention or treatment of stroke, and a method for promoting the production of microRNAs of stem cell-derived microvesicles and enhancing efficacy, and a method for promoting the production of stem cell-derived microvesicles and microRNAs within the microvesicles and enhancing the efficacy of stem cells and microvesicles thereof by 3-dimensionally culturing or ischemically stimulating stem cells.

BACKGROUND

Recently, various clinical trials have been conducted on incurable diseases such as stroke, spinal cord injury, multiple sclerosis, Alzheimer's disease, liver cirrhosis, myocardial infarction, renal disease, and graft versus host disease using mesenchymal stem cells (MSCs). Although positive clinical results have been reported to date, a therapeutic method using stem cells still has several problems for clinical application. First, in the case of cell therapeutic agents, there is a risk of tumor formation after engraftment of stem cells in tissues, and second, in the case of stem cells, cerebral infarction may occur due to an artery occlusion likely induced by the large size of the stem cells, and third, in the case of stem cells, the stem cells easily move into the brain when the brain-blood vessel barrier is open as in an acute stage, but in a chronic stage, movement of the stem cells is limited due to large sizes thereof. Finally, in the case of cell therapeutic agents, there is a limitation in inducing the propensity of cells that are specialized with a desired propensity.

Recently, as there has been an increasing number of reports that the clinical usefulness of mesenchymal stem cells is mainly caused by the paracrine effect, microvesicles (MV) secreted from stem cells have attracted attention in the field of regenerative medicine because the microvesicles mediate various effects through the paracrine thereof. Microvesicles refer to small vesicles with a diameter of 0.1 to 1 µm, in which a part of a cell membrane such as endothelial cells and platelets is released into the blood, and microvesicles derived from stem cells contain not only receptors and proteins, but also nuclear components, and thus, are known to mediate intercellular communication. Further, stem cell-derived microvesicles have the following important characteristics as an alternative to current stem cell transplantation treatment methods (Nephrol. Dial. Transplant. 27, 3037-3042 (2012)). Specifically, a vesicle structure having a nano size and including lipids is safer and more advantageous for the long-term blood circulation and the long-distance treatment activity than MSCs, and stem cell membrane proteins present on the surface of microvesicles may impart an ability to target a disease like injected stem cells, contain relatively less animal sera than stem cells, and thus has an advantage in that a risk of symptoms (zoonosis) caused by animal serum infection may also be eliminated.

However, since methods for mass-isolating and obtaining MSC-derived microvesicles, and the like have not yet been established for using the MSC-derived microvesicles for study and clinical purposes, this is a major limiting factor in developing stem cell-derived microvesicles as a medicinal product, and there are not enough study results on a method capable of further enhancing the efficacy thereof, and thus, there is a need for studies on this.

SUMMARY

Thus, the present inventors have made intensive studies to develop a method capable of solving the aforementioned problem, and as a result, experimentally confirmed that when stem cells are dynamically 3-dimensionally cultured or an ischemia stimulus is applied to stem cells by preparing a PEG hydrogel microwell array, the production of stem cell-derived microvesicles containing large amounts of various therapeutic materials including microRNAs and exhibiting neurogenesis and angiogenesis effects, and the like is promoted, thereby completing the present invention based on this.

Thus, the present invention provides a pharmaceutical composition for preventing or treating stroke, including stem cell-derived microvesicles with enhanced expression levels of one or more selected from the group consisting of microRNA-137 (miR-137), microRNA-184 (miR-184), and microRNA-210 (miR-210).

Further, another object of the present invention is to provide a method for promoting the production of microRNAs (miRNAs) in stem cell-derived microvesicles, including a step of 3-dimensionally culturing stem cells.

In addition, still another object of the present invention is to provide a method for promoting the production of microRNAs (miRNAs) in stem cell-derived microvesicles, including a step of ischemically stimulating stem cells.

Furthermore, yet another object of the present invention is to provide a method for enhancing the efficacy of stem cells or microvesicles isolated therefrom, including a step of 3-dimensionally culturing stem cells.

Further, yet another object of the present invention is to provide a method for enhancing the efficacy of stem cells or microvesicles isolated therefrom, including a step of ischemically stimulating stem cells.

However, technical problems to be achieved by the present invention are not limited to the aforementioned problems, and other problems that are not mentioned may be clearly understood by those skilled in the art from the following description.

To achieve the objects of the present invention as described above, the present invention provides a pharmaceutical composition for preventing or treating stroke, including stem cell-derived microvesicles with enhanced expression levels of one or more selected from the group consisting of microRNA-137 (miR-137), microRNA-184 (miR-184), and microRNA-210 (miR-210).

In addition, the present invention provides a method for promoting the production of microRNAs in stem cell-derived microvesicles, including a step of 3-dimensionally culturing stem cells.

Furthermore, the present invention provides a method for promoting the production of microRNAs in stem cell-derived microvesicles, including a step of ischemically stimulating stem cells.

As an embodiment of the present invention, the microRNA may be one or more selected from the group consisting of miR-137, miR-184, and miR-210.

As another embodiment of the present invention, the stem cell may be an embryonic stem cell, an induced pluripotent stem cell (iPSC), or an adult stem cell.

As still another embodiment of the present invention, the adult stem cell may be one or more adult stem cells selected from the group consisting of a mesenchymal stem cell, a human tissue-derived mesenchymal stromal cell, a human tissue-derived mesenchymal stem cell, and a multipotent stem cell.

As yet another embodiment of the present invention, the 3-dimensional culture may culture cells for 5 days to 9 days while performing rotation shaking in an incubator at 20 to 40 rpm 6 hours to 18 hours after aliquoting cells.

As yet another embodiment of the present invention, the ischemic stimulation may be caused by treatment of an ischemic individual with a brain tissue extract.

As yet another embodiment of the present invention, the ischemic stimulation may be performed for 12 hours to 48 hours.

Further, the present invention provides a method for enhancing the efficacy of stem cells or microvesicles isolated therefrom, including a step of 3-dimensionally culturing stem cells.

In addition, the present invention provides a method for enhancing the efficacy of stem cells or microvesicles isolated therefrom, including a step of ischemically stimulating stem cells.

As an embodiment of the present invention, the efficacy enhancement may be an enhanced expression of a growth factor, a cytokine, or a microRNA in stem cells.

As another embodiment of the present invention, the growth factor may be one or more selected from the group consisting of a fibroblast growth factor (FGF), a hepatocyte growth factor (HGF), a vascular endothelial growth factor (VEGF), a transforming growth factor beta (TGFβ), and bone morphogenetic protein 2 (BMP2).

As still another embodiment of the present invention, the cytokine may be one or more selected from the group consisting of CH13L1, CD105, CD147, ICAM-1, IP-10, MIP-β, IL-6, IL-8, GRO, TIMP-1, and SerpineE1.

As yet another embodiment of the present invention, the microRNA may be one or more selected from the group consisting of miR-137, miR-184, and miR-210.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 4C is a result of comparing the total concentration of proteins in microvesicles produced by each culture method on day 7 of the culture by correcting the total concentration with a predetermined number of cells;

DETAILED DESCRIPTION

Figure 1:
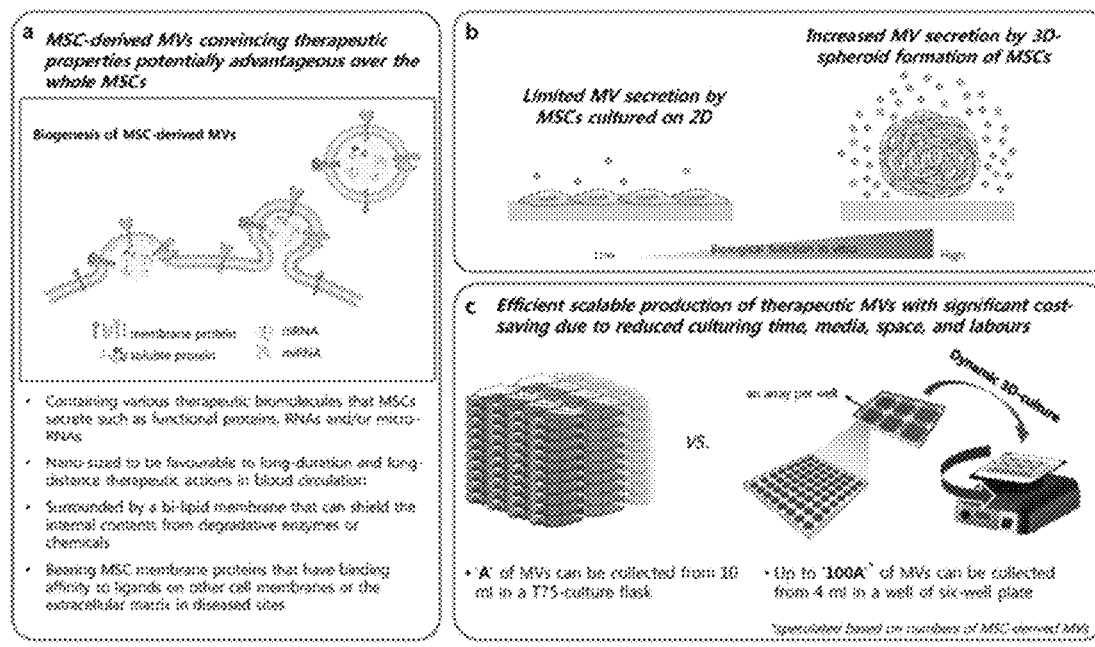
FIG. 1 is a pictorial illustration of the overall content of the 3D stem cell culture method and effect according to the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present inventors experimentally confirmed that when stem cells were dynamically 3-dimensionally cultured by preparing a PEG hydrogel microwell array, or an ischemic stimulation was applied to stem cells, the production of various therapeutic materials including stem cell-derived microvesicles and therapeutic microRNAs in the microvesicles was promoted, and there was an effect of substantially stimulating angiogenesis and neurogenesis by the stem cell-derived microvesicles, thereby completing the present invention based on this.

Thus, the present invention provides a pharmaceutical composition for preventing or treating stroke, including stem cell-derived microvesicles with enhanced expression levels of one or more selected from the group consisting of microRNA-137 (miR-137), microRNA-184 (miR-184), and microRNA-210 (miR-210).

In addition, the present invention provides a method for promoting the production of microRNAs in stem cell-derived microvesicles, including a step of 3-dimensionally culturing stem cells.

Furthermore, the present invention provides a method for promoting the production of microRNAs in stem cell-derived microvesicles, including a step of ischemically stimulating stem cells.

The microRNA may be one or more selected from the group consisting of miR-137, miR-184, and miR-210.

The present inventors found through the Examples that the production of stem cell-derived microvesicles and microRNAs in the microvesicles could be promoted by the 3D culture method and the ischemic stimulation according to the present invention, and accordingly, the efficacy of the stem cells and the microvesicles thereof could be enhanced.

In an example of the present invention, a PEG hydrogel microwell array was prepared for the 3D culturing according to the present invention, and 3D culturing was performed while performing rotation shaking at a predetermined speed in an incubator for 7 days after the spontaneous formation of spheroids was induced by aliquoting mesenchymal stem cells (MSCs) into each of the microwells. As a result, it was confirmed that the stem cells were densely packed, constituted spheroids, and secreted an extracellular matrix, and most cells constituting the spheroids survived. Further, as a result of observing the proliferation of cells according to culture time while performing the 2D or 3D culture with shaking or without shaking, it was confirmed that in the case of the 3D culture according to the present invention, the initial number of cells was maintained without an increase in the number of cells until day 7 of the culture (see Example 1).

In another example of the present invention, as a result of analyzing a change in expression profile of 84 genes associated with characteristics of mesenchymal stem cells after the MSCs were statically 2D cultured, or dynamically 3D cultured by the method according to the present invention, it was observed that the expression of various genes was upregulated or downregulated, and through this analysis, it could be seen that the differentiation potential for cartilage formation and bone formation was remarkably improved in the 3D cultured MSCs according to the present invention (see Example 2).

In still another example of the present invention, as a result of measuring the amount of microvesicles produced and the total amount of proteins in the microvesicles by isolating microvesicles from the MSCs cultured by each culture method after performing the dynamic 3D culture according to the present invention and culturing the MSCs by another culture method in the related art as described above, it was confirmed that when the MSCs were cultured by the method according to the present invention, a remarkably high amount of microvesicles was produced as compared to the other methods (see Example 3).

In yet another example of the present invention, after the MSC-derived microvesicles cultured by the dynamic 3D culture method according to the present invention and the MSC-derived microvesicles ischemically stimulated by treating stem cells with an ischemic brain extract were each obtained, therapeutic materials contained in the microvesicles were analyzed. As a result, there was a difference in expression level between both of the two types of microvesicles, but on the whole, it was confirmed that a large amount of cytokines associated with immunoregulation and neovascularization was contained. Further, it was confirmed that microRNAs known to be associated with neurogenesis and neovascularization were also present in a large amount (see Example 4).

In yet another example of the present invention, the effects of stimulating angiogenesis and neurogenesis of each of the dynamically 3D cultured MSC-derived microvesicles according to the present invention and the ischemic brain extract-treated MSC-derived microvesicles were verified. As a result, it was confirmed that both of the two types of microvesicles stimulated the tube formation of human umbilical vein endothelial cells, the proliferation of neural stem cells, and the differentiation into nerve cells at significant levels, and it was also confirmed that the 3D culture had a significant effect as compared to the 2D culture. Furthermore, it was confirmed that the dynamically 3D cultured MSC-derived microvesicles and the ischemic brain extract-treated MSC-derived microvesicles exhibited the effects of stimulating angiogenesis and neurogenesis at a level similar to or a level higher than the case where cells were transfected with miR-210 and miR-184 known to be associated with angiogenesis and neurogenesis, and inhibited the expression of Ephrin A3 and Numbl which are a target protein of the miRNAs, respectively (see Example 5).

The aforementioned results demonstrate that it is possible to promote the production of microvesicles and microRNAs in the microvesicles by 3D-culturing stem cells by the method according to the present invention or ischemically stimulating stem cells, and accordingly, it is possible to enhance the efficacy of stem cells or the stem cell-derived microvesicles.

In the present invention, the stem cell may be an embryonic stem cell, an induced pluripotent stem cell (iPSC), or an adult stem cell, and preferably, the adult stem cell may be one or more selected from the group consisting of a mesenchymal stem cell, a human tissue-derived mesenchymal stromal cell, a human tissue-derived mesenchymal stem cell, and a multipotent stem cell, but is not limited thereto.

The contents of the overall concept and effect of the dynamic 3D-MSC culture method are illustrated in FIG. 1 with a drawing, and there is an advantage in that stem cell-derived microvesicles may be obtained in a large amount by the method which is a simple and efficient method. Specifically, the dynamic 3D culture is performed in the PEG hydrogel microwell prepared in the present invention, more specifically, may be a culture for 5 days to 9 days while performing rotation shaking in an incubator at 20 to 40 rpm, more preferably 30 rpm after aliquoting a predetermined amount of stem cells into the microwell and inducing the spontaneous formation of spheroids for 6 hours to 18 hours, more preferably about 12 hours, and more preferably, includes a culturing procedure for about 6 days to 7 days.

The ischemic stimulation of stem cells according to the present invention is performed through the procedure of treating the stem cells with a brain tissue extract of a brain ischemic-induced individual, and the ischemic stimulation was induced by treating mesenchymal stem cells with an ischemic brain extract and culturing the mesenchymal stem cells for 12 hours to 48 hours, more preferably 24 hours.

In the present invention, the efficacy enhancement may include an enhancement in expression of a growth factor, a cytokine, or a microRNA in stem cells, and the growth factor may be one or more selected from the group consisting of a fibroblast growth factor (FGF), a hepatocyte growth factor (HGF), a vascular endothelial growth factor (VEGF), a transforming growth factor beta (TGFβ), and bone morphogenetic protein 2 (BMP2), the cytokine may be one or more selected from the group consisting of CH13L1, CD105, CD147, ICAM-1, IP-10, MIP-1β, IL-6, IL-8, GRO, TIMP-1, and SerpineE1, and the microRNA may be one or more selected from the group consisting of miR-137, miR-184, and miR-210, but are not limited thereto.

Hereinafter, preferred examples for helping the understanding of the present invention will be suggested. However, the following examples are provided only to more easily understand the present invention, and the contents of the present invention are not limited by the following examples.

EXAMPLES

Figure 2A:
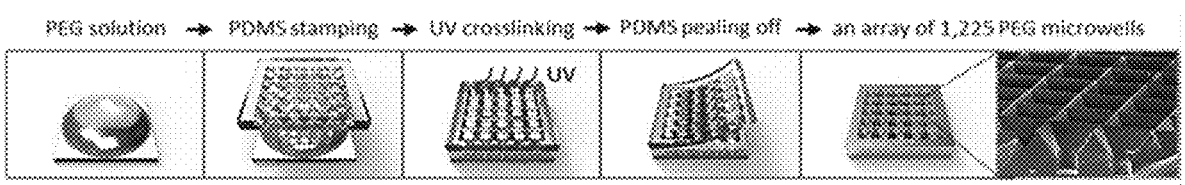
FIG. 2A is a view illustrating a procedure of preparing a PEG microwell array used for the 3D-culture of MSCs.
Figure 2B:
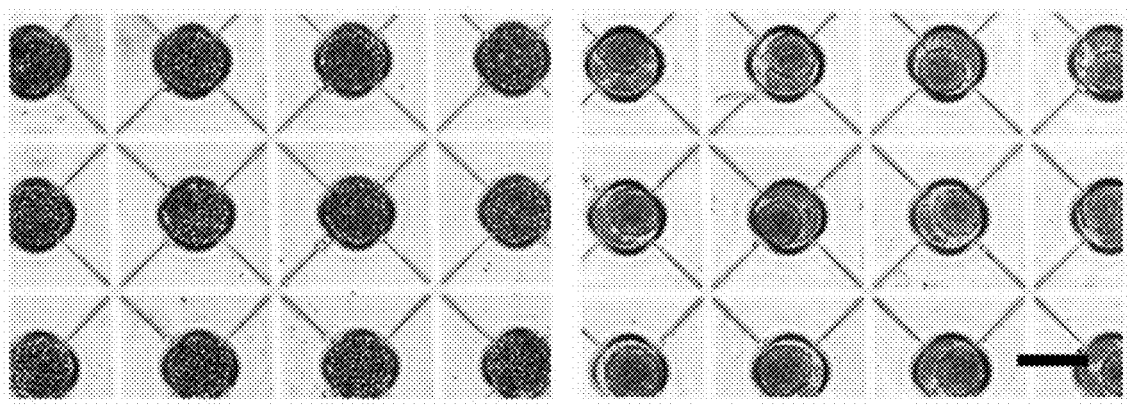
FIG. 2B is a result showing that MSCs are aliquoted at a predetermined density, and then spherical cell aggregates are formed within 12 hours.

Example 1. 3D Culture of Mesenchymal Stem Cells 1-1. Formation and Culture of Size-Limited hMSC-Spheroids For a 3D cell culture of mesenchymal stem cells, a polyethylene glycol (PEG) microwell array was manufactured by a soft-lithography process using a poly(dimethylsiloxane) (PDMS) mold, as illustrated in FIG. 2A, and thereafter, the polyethylene glycol (PEG) microwell array was UV-sterilized for 20 minutes after disinfecting the array with 70% ethanol and adding PBS thereto. The customized microwell array manufactured by the present inventors consisted of cylindrical microwells with inverted pyramidal openings, and thus blocked cell loss when hMSC-spheroids were cultured in a large amount, and an optimized PEG hydrogel soft-lithography technology prevented cells from being attached to a microwell substrate. In addition, in order to uniformly control the size of the hMSC-spheroid and the number of cells, a microwell array including 1,225 microwells each with a diameter of 200 μm was manufactured in a size of 20×20 mm so as to fit each well of a commercially available 6-well plate. Thereafter, in order to aliquot cells into the microwell, hMSCs were aliquoted at a density of $5 \times 10^5$ cells/array (~400 cells/microwell) by treating human-derived mesenchymal stem cells (hMSCs, PT2501, Lonza, Basel, Switzerland) cultured in a DMEM medium supplemented with 10% fetal bovine serum (FBS) or exosome-free FBS and a 1% antibiotic with trypsin to collect and count cells, and then cultured in a $CO_2$ incubator (37° C., 5% $CO_2$), and as illustrated in FIG. 2B, it was confirmed that spherical cell aggregates were spontaneously formed within 12 hours after the aliquoting. The hMSC-spheroids were uniformly formed with a diameter of about 150 μm, which is smaller than the size of the microwell, and then additionally cultured (3D w/shaking) at 30 rpm in an orbital shaker in the $CO_2$ incubator for 7 days.

1-2. Observation of Spheroids and Analysis of Ability to Proliferate Cells Through Dynamic 3D Culture (3D w/Shaking)

Figure 2C:
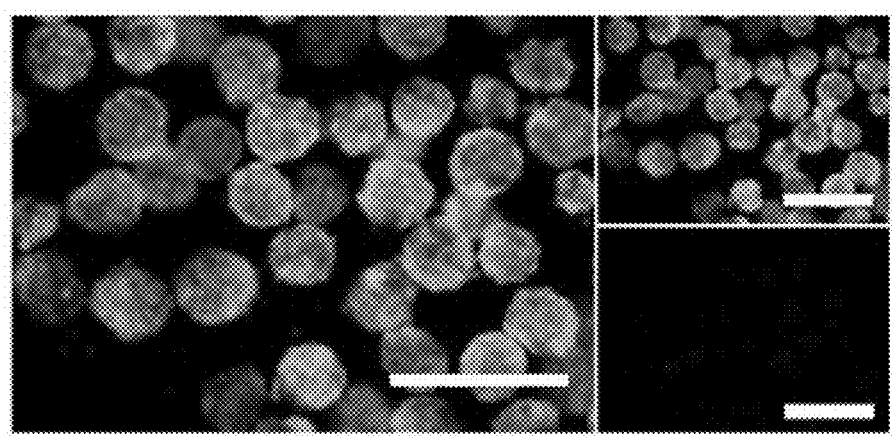
FIG. 2C is a result confirming the survival of cells for the MSC-spheroids on day 5 after a dynamic 3D culture.

For the hMSCs cultured by the method in Example 1-1, first, an experiment was performed using a LIVE/DEAD viability/cytotoxicity kit (Invitrogen, Carlsbad, Calif., USA) on day 5 of the culture in order to verify whether cells constituting the spheroid survived. As a result, as illustrated in FIG. 2C, it was confirmed that most cells survived.

Figure 2D:
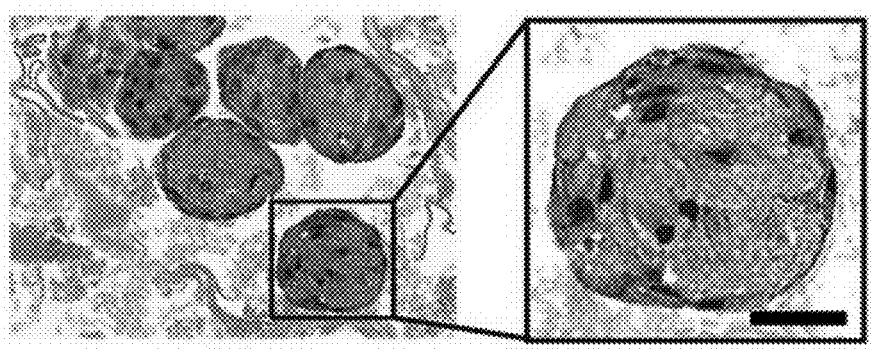
FIGS. 2D and 2E are results of performing hematoxylin and eosin (H&E) staining and Masson trichrome (M&T) staining, respectively.
Figure 2E:
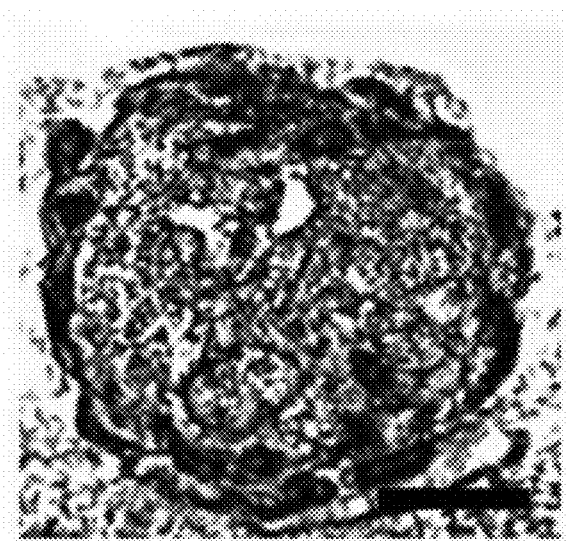

In addition, as a result of performing haematoxylin & eosin (H&E) staining and Masson trichrome (M&T) staining on the hMSC-spheroids on day 5 of the culture, as illustrated in FIGS. 2D and 2E, it could be seen that hMSCs densely aggregated to form spheroids, and secreted an extracellular matrix (ECM).

Figure 2F:
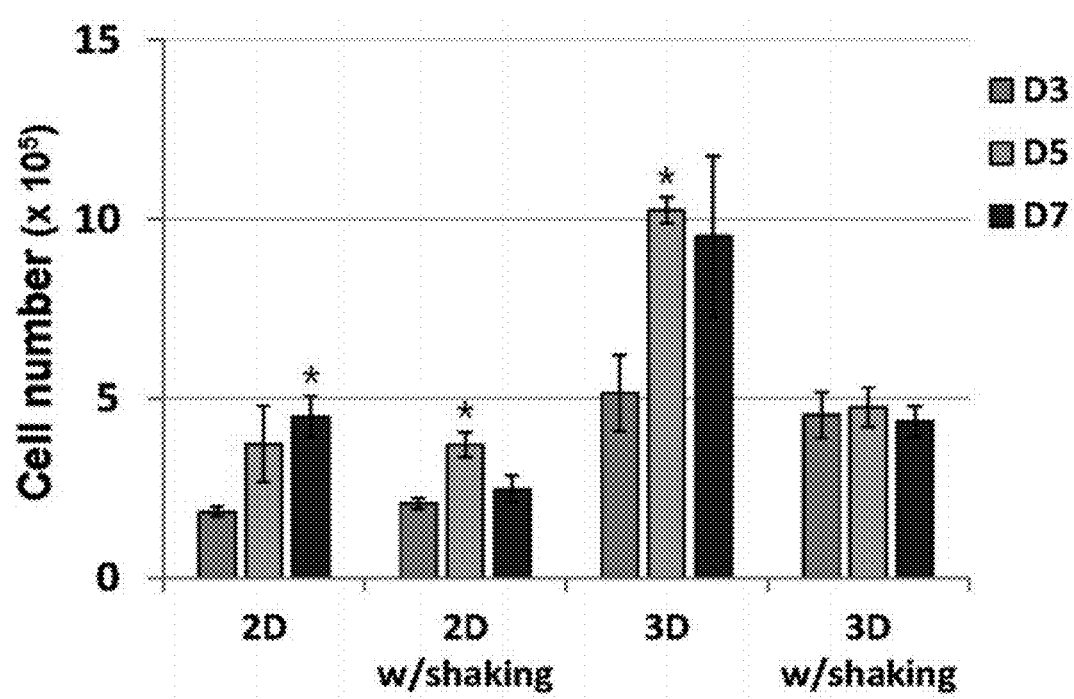
FIG. 2F is a result of comparing the abilities of MSC to proliferate by measuring the number of cells on day 3 (D3), day 5 (D5), and day 7 (D7) of the culture while statically 2D culturing MSCs, dynamically 2D culturing MSCs with continuous shaking (2D w/shaking), statically 3D culturing MSCs, and dynamically 3D culturing MSCs (3D w/shaking)

Furthermore, in order to examine the ability of hMSCs to proliferate, the number of cells was measured on day 3 (D3), day 5 (D5), and day 7 (D7) using a DNA quantification assay kit (CyQUANT NF Cell Proliferation Assay Kit, Invitrogen) while culturing hMSCs by a 2D culture method with shaking or without shaking (2D or 2D w/shaking) or a static 3D culture method without shaking along with the dynamic 3D culture method. As a result, as illustrated in FIG. 2F, it was shown that when hMSCs were cultured by the static 2D culture method (2D) without shaking, the number of hMSCs was increased according to the culture time, and when hMSCs were cultured by the dynamic 2D culture method (2D w/shaking), the number of cells was decreased after about 5 days due to the vulnerability of attached cells to shear stress continuously applied. On the other hand, in the case of the static 3D culture method, hMSCs were allowed to form spheroids in the microwells, and then transferred to a petri dish, and then cultured without shaking, and interestingly, it was observed that hMSC-spheroids were attached to the bottom of the dish from day 1 of the culture and proliferated to a neighboring region. For this phenomenon, it was assumed that the ECMs secreted from hMSCs at the initial stage diffused onto the petri dish, and thereafter, hMSCs constituting the spheroid were attached thereon. Accordingly, in the case of the static 3D culture (3D), it was shown that the number of hMSCs on day 5 (D5) of the culture was almost double the initial number of cells, and was maintained until day 7 of the culture. In contrast, in the case of the dynamic 3D culture (3D w/shaking) according to the present invention, it was shown the number of cells was not decreased during the culture period. This result coincided with a previous study result that MSC-spheroids cultured in a suspension using a medium supplemented with fetal bovine serum (FBS) maintained the initial number of cells while maintaining the same biological characteristics as those of stem cells.

Figure 3A:
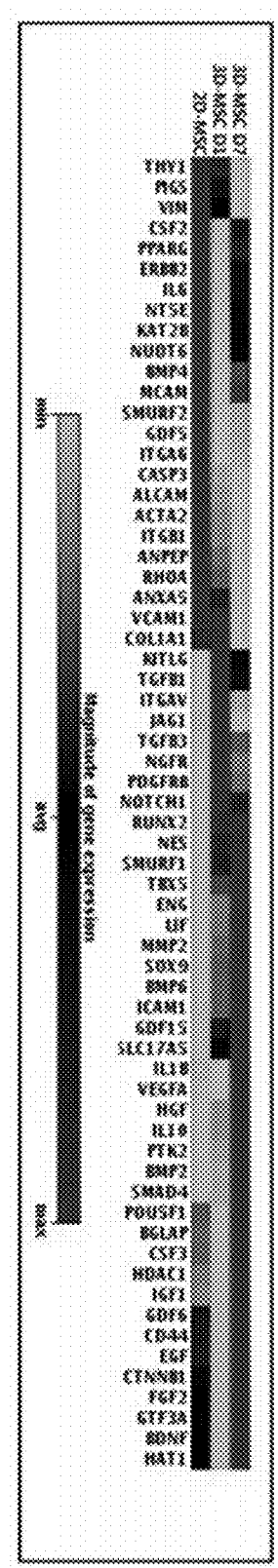
FIG. 3A is a result presented as a cluster gram by measuring the expression levels of 84 major genes associated with characteristics of the MSCs cultured by a 2D culturing or dynamic 3D culture method (on day 1 and day 7) through PCR, FIG. 3B compares and illustrates the expression levels of genes associated with the stemness of MSCs and the MSC marker in each experimental group.
Figure 3B:
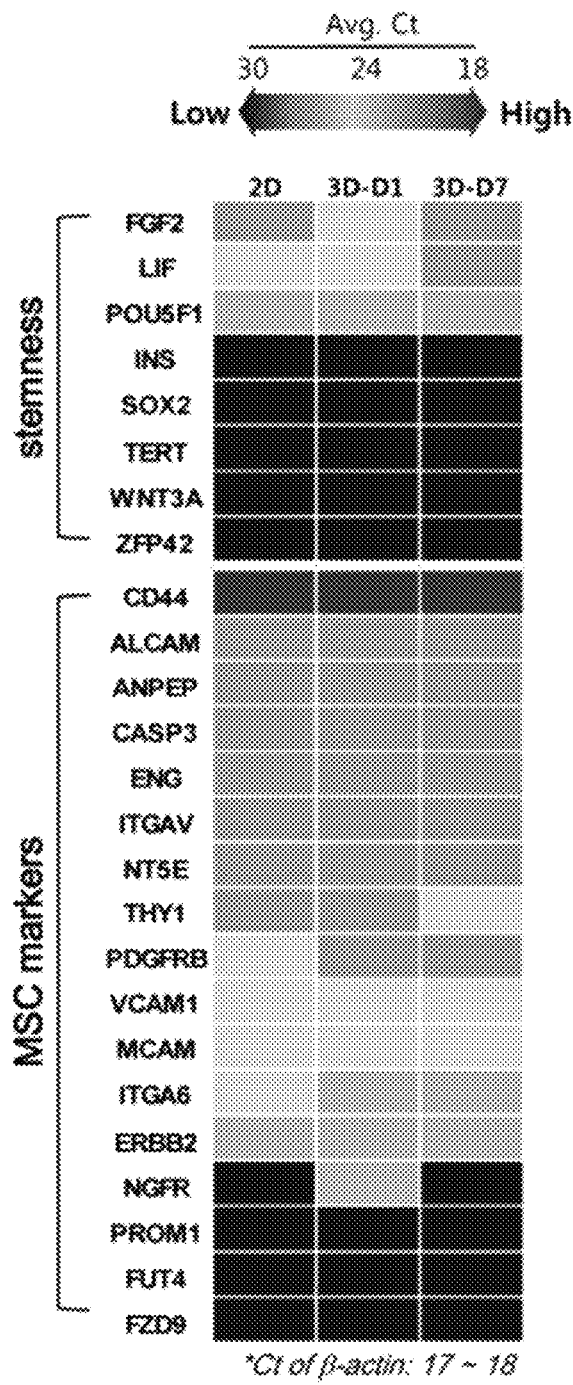
FIG. 3C illustrates the expression of genes exhibiting characteristics of hMSCs with an average Ct value of less than 30 expressed in a scatter plot and the comparison of the expressions among experimental groups.

Example 2. Analysis of Gene Expression Profile of Dynamically 3D Cultured MSC-Spheroids Next, the present inventors performed expression profiling of 84 major genes associated with general characteristics of hMSCs through PCR in order to verify the difference between stem cell characteristics of the 2D cultured or dynamically 3D cultured hMSCs, and FIG. 3A illustrates relatively different gene expressions between the 2D cultured MSCs and the dynamically 3D cultured MSCs using a cluster gram of the PCR array. In the case of the 3D culture, hMSCs on day 1 of the culture (3D-MSC D1) exhibited a temporary change in gene expression profile because these cells were in the process of forming 3D-spheroids for 3 days of the culture. Further, as illustrated in FIG. 3B, genes associated with stemness, such as FGF2, LIF, and POU5F1 were shown to be highly expressed in the case of all the culture methods (2D, 3D-D1, and 3D-D7), and among them, the expression of FGF2 and LIF was generally decreased slightly during the formation of hMSC-spheroids, and then increased again by the 3D culture (3D-D7). In addition, various hMSC marker genes were shown to be highly expressed in the dynamic 3D-MSCs as compared to 2D-MSCs.

Figure 3C:
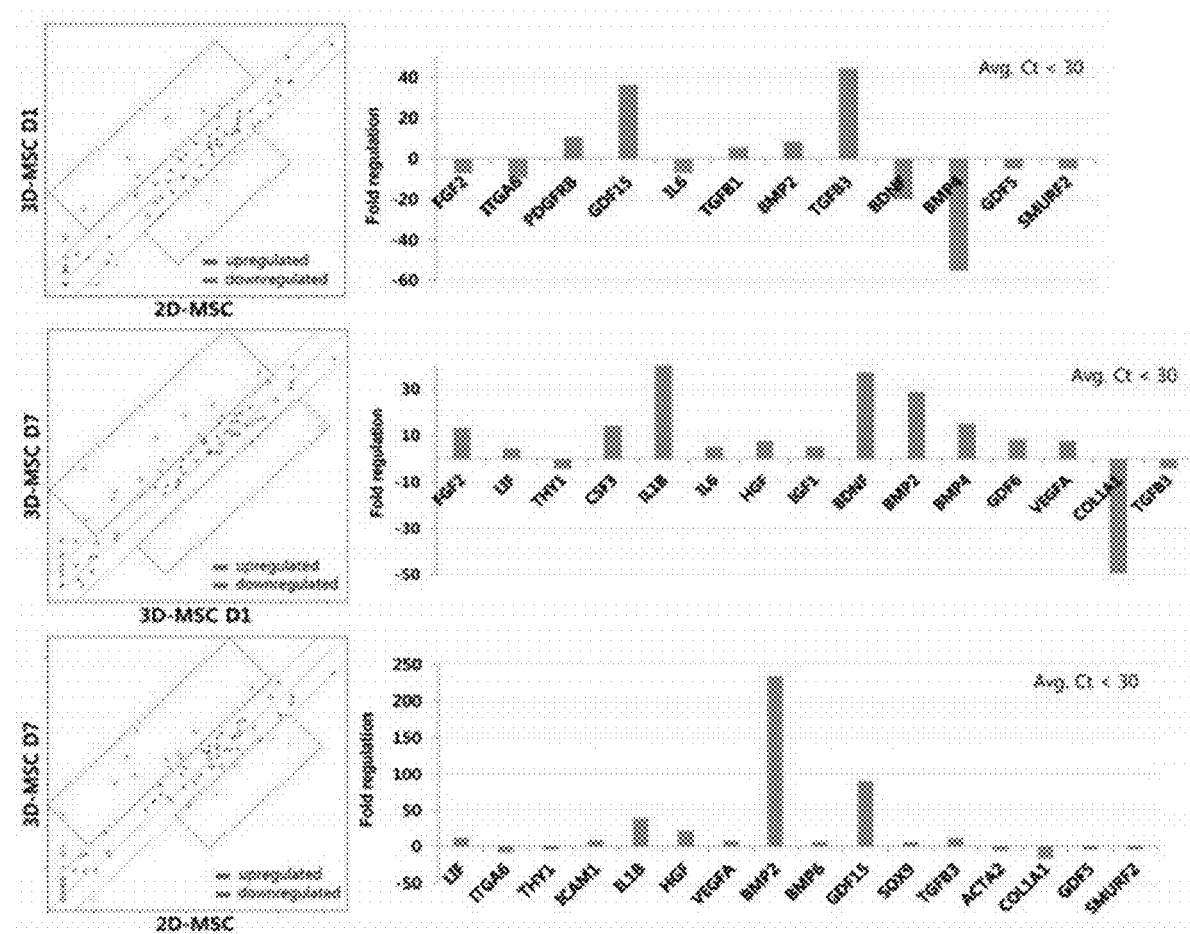

Furthermore, the expression of genes exhibiting characteristics of hMSCs with an average Ct value of less than 30 was expressed in a scatter plot, and the comparison of expressions among groups was performed. In this case, in order to avoid over-evaluation, it was not considered a significant difference when the expression was upregulated or downregulated by 30 times or less in the relative comparison. As a result of the analysis, as illustrated in FIG. 3C, on day 1 of hMSC-spheroid formation (3D-MSC D1), the expression of GDF15 and TGFB3 was shown to be upregulated by about 40 times as compared to the 2D cultured control (2D-MSC), whereas the expression of BMP4 was shown to be downregulated by about 60 times. In the case of comparison between the dynamically 3D cultured hMSCs, it was shown that the expression of IL1B, BDNF, and BMP2 was upregulated by 30 times or more on day 7 of the culture (3D-MSC D7), and the expression of COL1A1 was downregulated by about 50 times as compared to that of the initial stage which is day 1 of the culture (3D-MSC D1). A remarkable decrease in COL1A1 as the stage proceeded from D1 to D7 means that a decrease in ECM secretion during the initial stage of the culture is required for a structural configuration of 3D hMSC aggregates. Next, it was shown that when 3D-MSCs were compared with 2D-MSCs, the expression of IL1B and GDF15 was upregulated by about 40 times and about 90 times, respectively, and particularly, the expression of BMP2 was upregulated at a high level by up to about 230 times. Through these results, it could be seen that in the 3D cultured MSCs, the differentiation potential for cartilage formation (upregulation of TGFB3) and bone formation (upregulation of BMP2) was remarkably improved, which coincides with previous study results.

Example 3. Analysis of Microvesicles Produced by Dynamic 3D-MSC Culture 3-1. Separation of Microvesicles from MSC In order to separate microvesicles from MSCs, after the culture solution of MSCs cultured by each method was collected, and then impurities were removed from the culture supernatant by centrifugation at low speed (2,500×g, 10° C., 10 minutes), high-speed centrifugation (14,000×g, 10° C., 10 minutes) was performed again, thereby obtaining stem cell-derived microvesicles.

3-2. Confirmation of Increase in Production of MSC-Derived Microvesicles

Figure 4A:
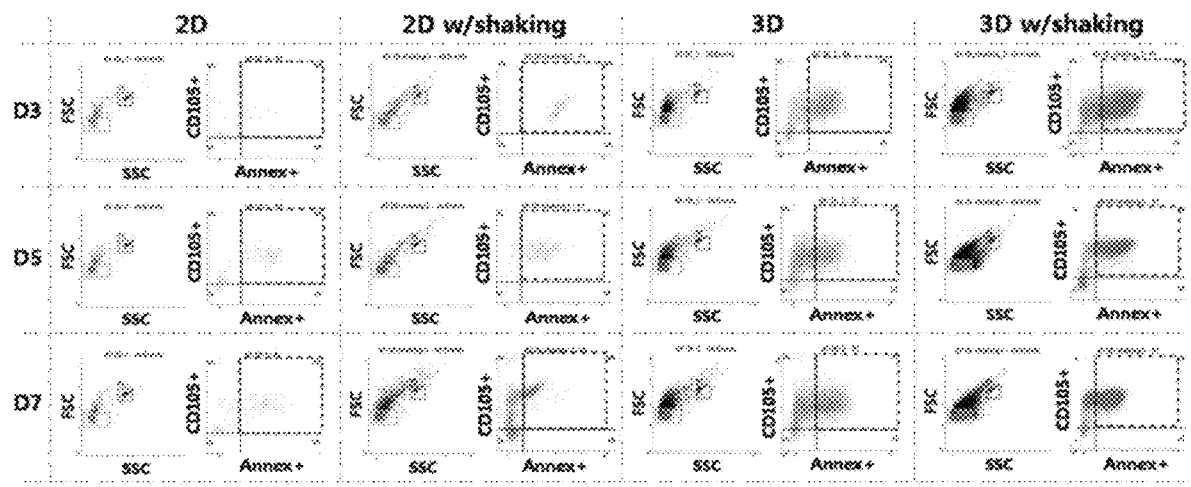
FIG. 4A is a result of performing flow cytometry by isolating microvesicles on day 3 (D3), day 5 (D5), and day 7 (D7) of the culture from the MSCs cultured by the static 2D culture, the dynamic 2D culture with continuous shaking (2D w/shaking), the static 3D culture, and the dynamic 3D culture (3D w/shaking), respectively.
Figure 4B:
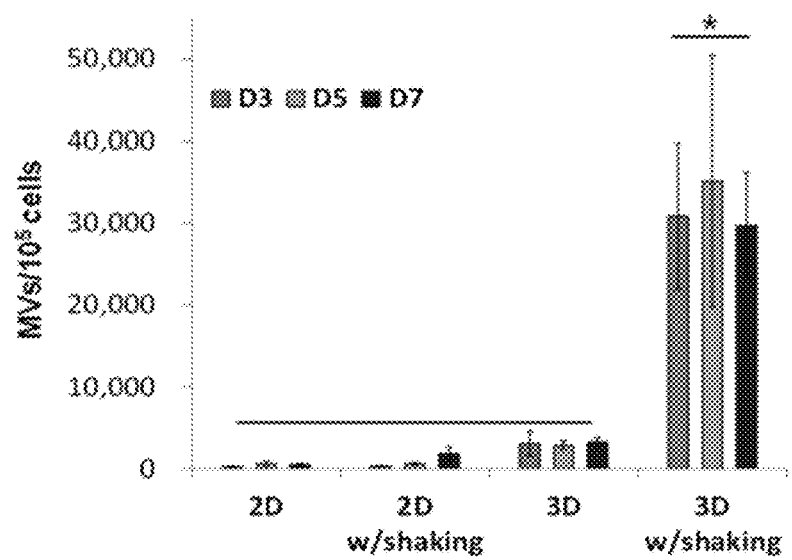
FIG. 4B is a result of comparing the amounts of microvesicles produced according to the culture time for each culture method by correcting the amounts with a predetermined number of cells.

The present inventors intended to measure the phenotype and amount of microvesicles isolated from MSCs respectively cultured by the static 2D culture (2D), the dynamic 2D culture (2D w/shaking), the static 3D culture (3D), and the dynamic 3D culture (3D w/shaking) methods using a flow cytometry method. For this purpose, as illustrated in FIG. 4A, on day 3 (D3), day 5 (D5), and day (D7) of the culture, particles with a size of 1.0 μm or less measured using standard-sized beads, and particles doubly positively stained with anti-CD105 (hMSC surface marker) and anti-annexin V (lipid surface marker) were counted as MSC-derived microvesicles. The counted point was used to calculate the absolute number of microvesicles, and the final number of microvesicles was corrected with the number of cells of the corresponding culture group. As a result, as illustrated in FIG. 4B, in the case of the dynamic 3D culture (3D w/shaking), the number of hMSC-derived microvesicles was measured to be the highest, showing that the number is about 100 times higher than that of the static 2D culture control in which a very small number of microvesicles were measured. In the case of the dynamic 2D culture (2D w/shaking), the number of collected microvesicles was not significant, but was shown to be higher than that of the static 2D culture, and the formation of hMSC-spheroids in the static culture did not increase a considerable amount, but was shown to increase the production of microvesicles, as observed in the case of the 3D culture (3D). In addition, as illustrated in FIG. 4C, a protein analysis result corrected with the number of cells of each culture group on day 7 of the culture supported the results, and in the case of the dynamic 3D culture as compared to the other groups, it was confirmed that the total concentration of proteins of the obtained microvesicles was significantly higher than those of the other groups. Furthermore, through the result obtained using the exosome-free FBS (Exo-free 3D-MVs), it was confirmed that the increase in production of MSC-derived microvesicles confirmed in the present experiment was not affected by particles included in FBS.

Example 4. Analysis of Expression of Therapeutic Material in MSC-Derived Microvesicles The present inventors intended to verify therapeutic characteristics of microvesicles isolated from the hMSCs cultured in large quantities by the dynamic 3D culture method by analyzing the microvesicles. Along with this, the present inventors confirmed that through previous studies, when MSCs were pre-treated with an ischemic brain extract, the efficacy of MSCs could be improved, and also intended to analyze the therapeutic characteristics of the ischemic brain extract-treated MSC-derived microvesicles by isolating the ischemic brain extract-treated MSC-derived microvesicles.

4-1. Preparation and Treatment of Ischemic Brain Extract

A transient middle cerebral artery occlusion (tMCAo) was induced in a rat for 90 minutes, and after 3 days, the damaged brain hemisphere tissue was ground at a concentration of 150 mg/ml along with the DMEM medium. Next, the ground tissue solution was centrifuged at 10,000×g for 10 minutes, and an ischemic brain extract (IBE) was obtained by taking the supernatant thereof, and the obtained ischemic brain extract was aliquoted into equivalent amounts and stored at −70° C. until the extract was used. Thereafter, in order to apply the ischemic stimulation to MSCs, impurities were removed by centrifugation of the stored ischemic brain extract at 2,500×g for 10 minutes, and then the resultant was diluted 5 times in DMEM, and then again centrifuged at 14,000×g for 45 minutes, and filtered with a 0.2 um filter. Bone marrow-derived adult stem cells (rMSCs) or hMSCs collected from the femur and tibia of 220 to 250 g Sprague-Dawley (SD) male rats were treated with the ischemic brain extract prepared by the method for 24 hours.

4-2. Confirmation of Levels of Therapeutic Materials in IBE-MVs and 3D-MVs

Figure 5A:
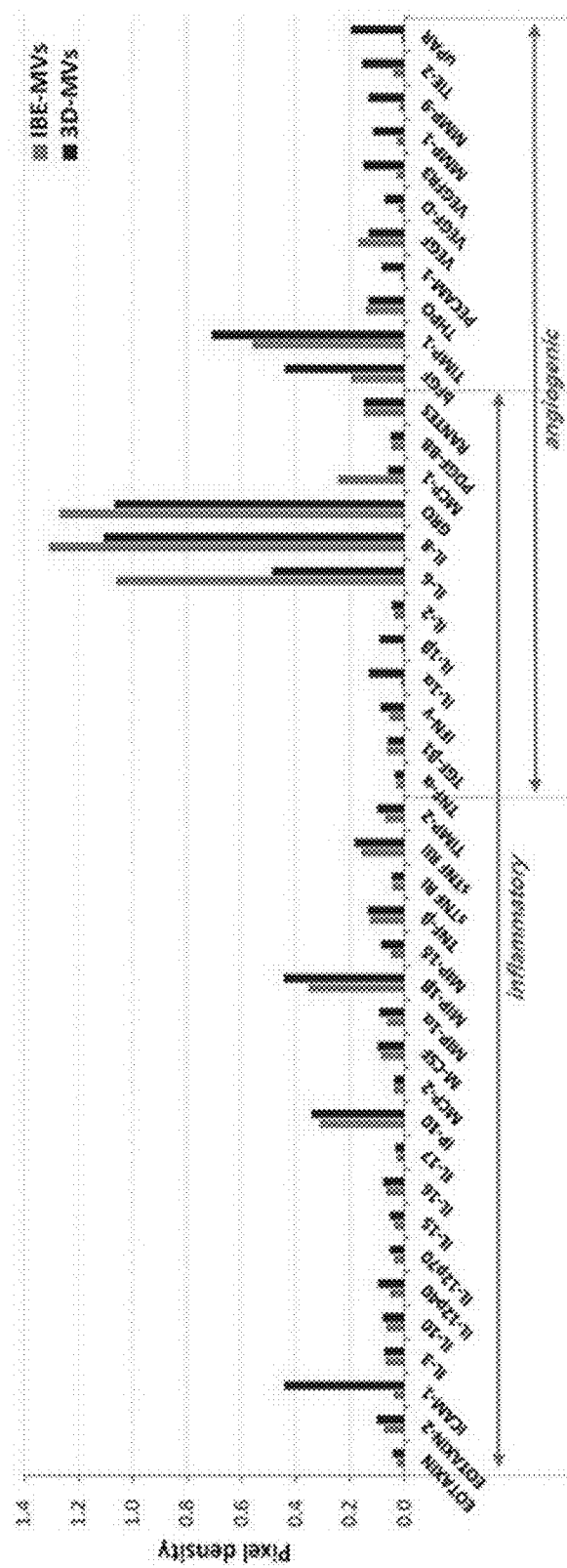
FIGS. 5A and 5B are results of measuring the contents of various cytokines in the two types of microvesicles.
Figure 5B:
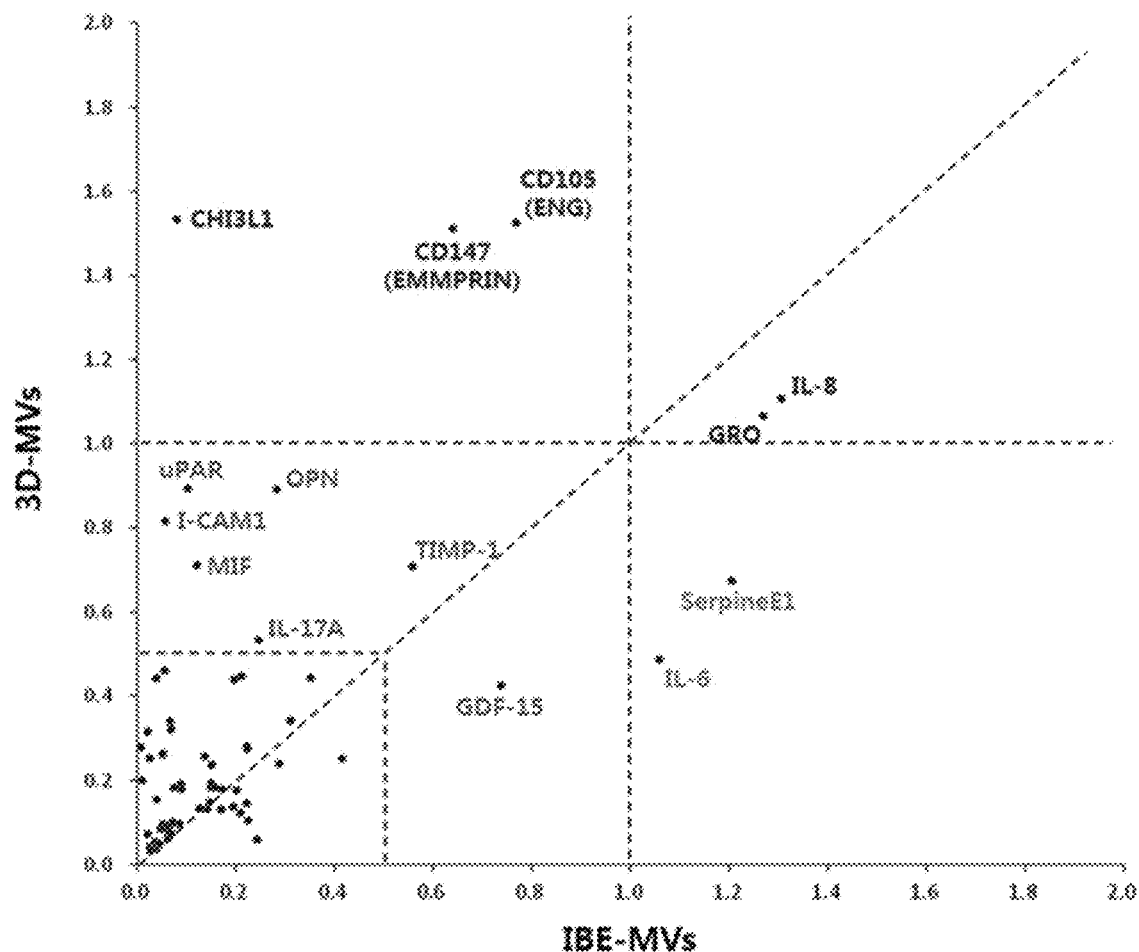

It was intended to examine whether a therapeutic material was included in the hMSC-derived microvesicles (3D-MVs) cultured by the dynamic 3D culture method and the ischemic brain extract-treated MSC-derived microvesicles (IBE-MVs). For this purpose, first, representative cytokines included in the microvesicles were analyzed using various cytokine array kits. As a result, as illustrated in FIGS. 5A and 5B, it was confirmed that various cytokines associated with immunoregulation and neovascularization were contained in IBE-MVs. Further, generally, cytokines detected in the IBE-MVs were also shown to be included in 3D-MVs. In particular, IP-10, MIP-1, βIL-8, GRO, and TIMP-1 were shown to be at high levels with slight differences in both IBE-MVs and 3D-MVs. In addition, some cytokines appeared differently in the two groups, ICAM-1, bFGF, CHI3L1, CD147, and CD105 were shown to be contained in large amounts in 3D-MVs, whereas IL-6 and SerpineE1 were shown to be contained in large amounts in IBE-MVs.

Figure 5C:
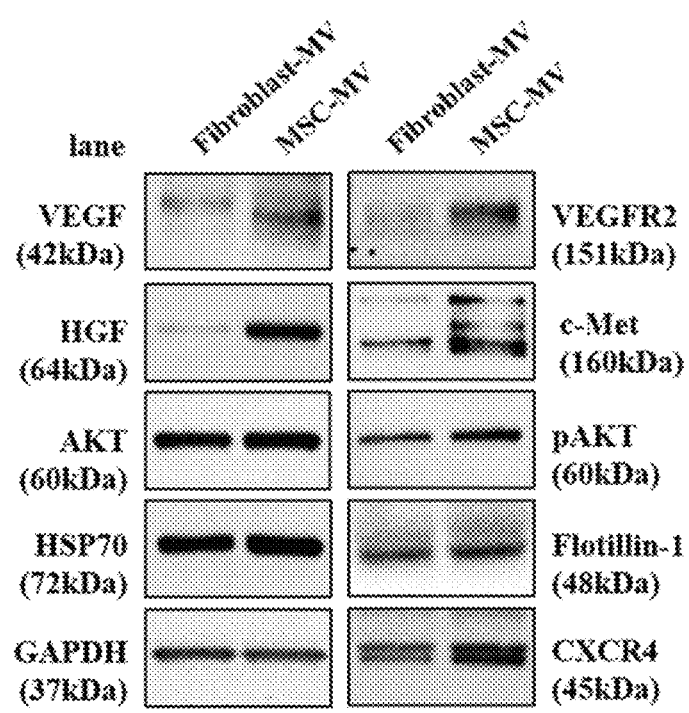
FIG. 5C is a result of comparing and measuring the expressions of growth factors associated with the treatment of stroke in ischemic brain extract-treated rMSC-derived microvesicles (MSC-MVs) and fibroblast-derived microvesicles (Fibroblast-MVs) by western blot.

In addition, the expressions of growth factors affecting stroke were compared with those of fibroblast-derived microvesicles by western blot by isolating microvesicles from the ischemic brain extract-treated mouse bone marrow-derived mesenchymal stem cells according to the method in Example 4-1. As a result, as illustrated in FIG. 5C, it was confirmed that Flotillin-1 and HSP70 proteins which are microvesicle markers were expressed in both of the two types of cell-derived microvesicles, and that the expression of proteins associated with the treatment of stroke was increased in mesenchymal stem cell-derived microvesicles (MSC-MVs) as compared to the ischemic brain extract-treated fibroblast-derived microvesicles (fibroblast-MVs).

4-3. Confirmation of Levels of Therapeutic microRNAs in IBE-MVs and 3D-MVs

Figure 6A:
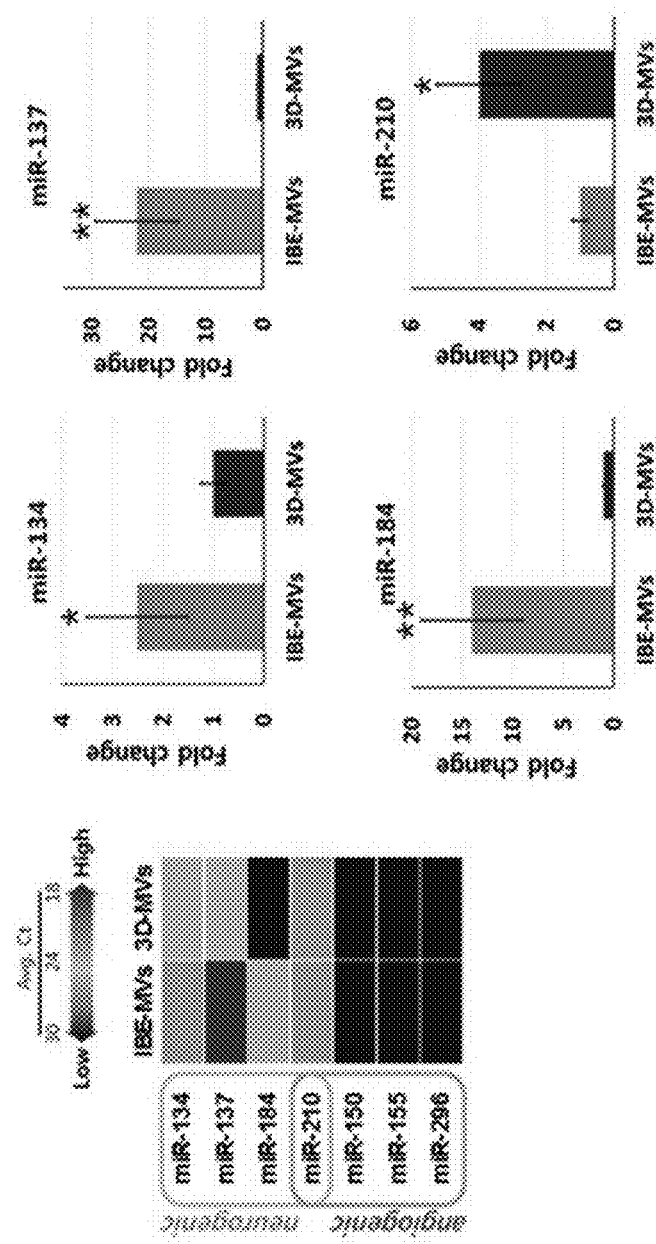
FIG. 6A is a result of measuring and comparing the expression levels of the microRNAs in the two types of microvesicles.

In addition to the result in Example 4-2, the present inventors analyzed the expression levels of microRNAs known to be important for neurogenesis and/or neovascularization signaling in the ischemic brain extract-treated hMSC-derived microvesicles and dynamically 3D cultured hMSC-derived microvesicles by performing qPCR. As a result, as illustrated in FIG. 6A, it was confirmed that miR-137 and miR-184 reported to be associated with neurogenesis were present in large amounts in the ischemic brain extract-treated hMSC-derived microvesicles (IBE-MVs), and that miR-210 known to be associated with both neurogenesis and neovascularization was shown to be expressed highly in both IBE-MVs and 3D-MVs, and was included in a relatively higher amount in 3D-MVs compared to IBE-MVs.

Figure 6B:
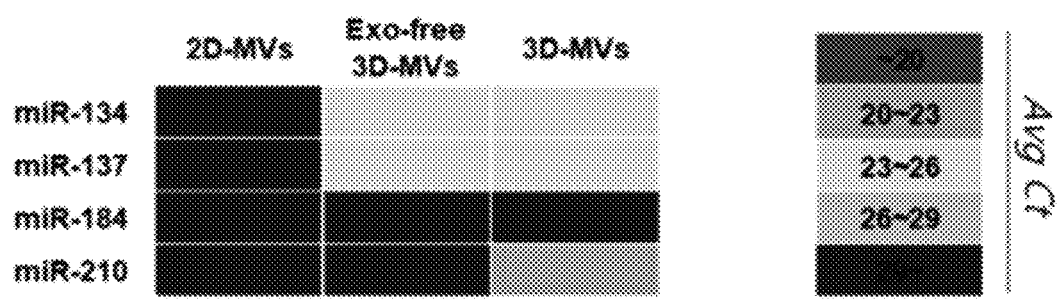
FIG. 6B is a result of measuring and comparing the expression levels of the microRNAs in the hMSC-derived microvesicles cultured by the 2D culture method, a dynamic 3D culture method using exosome-free FBS, and the dynamic 3D culture method (2D-MVs, Exo-free 3D-MVs, and 3D-MVs, respectively)

In addition to the result, in order to verify whether the 3D culture method is effective for increasing the expression of therapeutic microRNAs in the MSC-derived microvesicles, the contents of microRNAs in the hMSC-derived microvesicles (2D-MVs, Exo-free 3D-MVs, and 3D-MVs, respectively) cultured by the 2D culture method, the dynamic 3D culture method using exosome-free FBS, and the dynamic 3D culture method, respectively were compared. As a result, as illustrated in FIG. 6B, it was confirmed that in the case of the 2D culture method, all the therapeutic microRNAs were weakly expressed, whereas in the case of the two dynamic 3D cultures, miR-134 and miR-137 were shown to be expressed at high levels, and mir-210 was expressed at a high level in 3D-MVs.

Figure 6C:
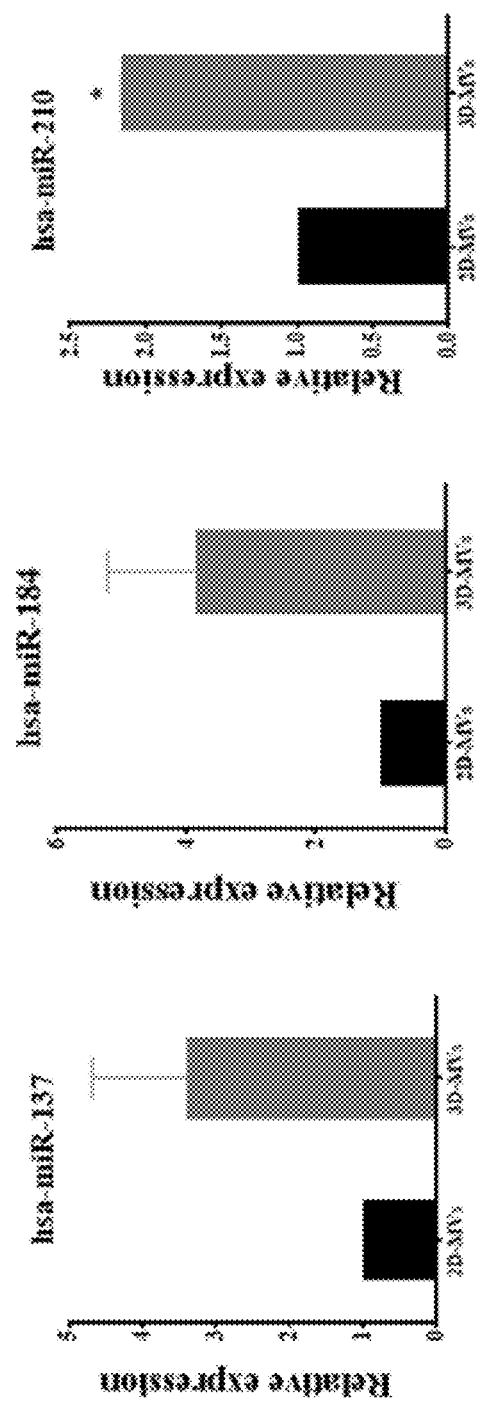
FIG. 6C is a result of comparing the expression levels of microRNAs in the hMSC-derived microvesicles cultured by the 2D culture method (2D-MVs) or the dynamic 3D culture method (3D-MVs)

In addition, the expression levels of miR137, miR-184, and miR-210 known to be important for angiogenesis and/or neurogenesis signaling in the hMSC-derived microvesicles (3D-MVs) cultured by the 2D culture method (2D-MVs) or the dynamic 3D culture method were analyzed. As a result, as illustrated in FIG. 6C, it was confirmed that miR137, miR-184, and miR-210 were expressed at higher levels in 3D-MVs than in 2D-MVs, and through this, it could be seen that the expression of the therapeutic microRNAs was specifically increased through the dynamic 3D culture.

Figure 6D:
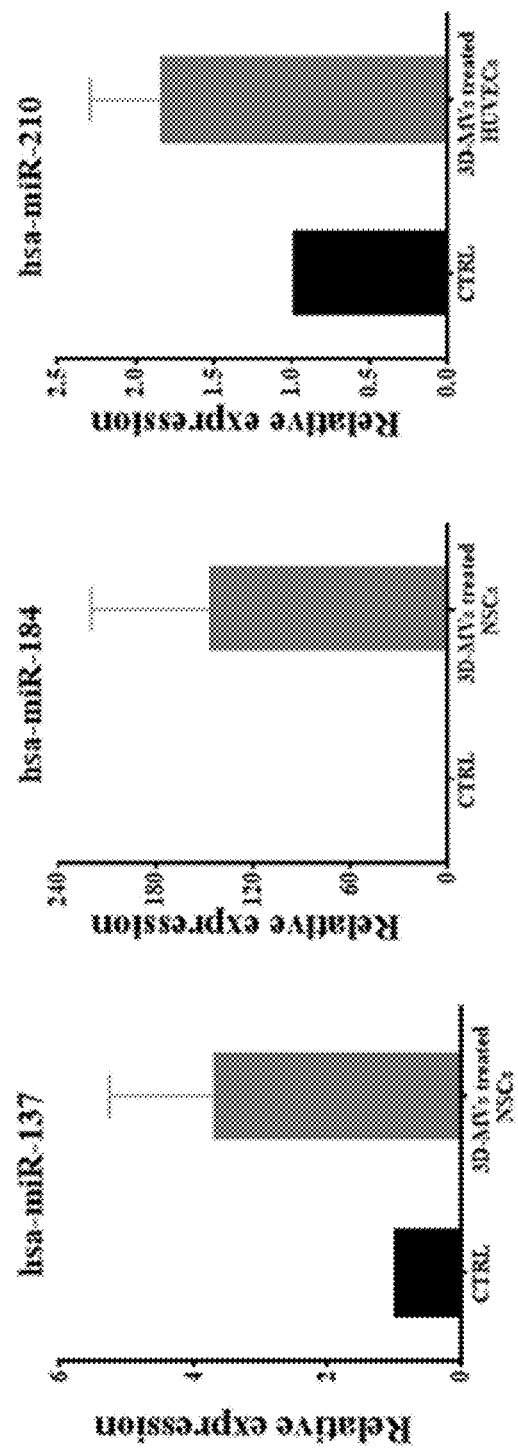
FIG. 6D is a result of treating 3D-MVs with human umbilical vein endothelial cells (HUVECs) or neural stem cells (NSCs) with 3D-MVs, and then analyzing the expression levels of microRNAs.

In addition, after human umbilical vein endothelial cells (HUVECs) or neural stem cells were treated with 3D-MVs, the expression levels of microRNAs were analyzed. As a result, as illustrated in FIG. 6D, it was confirmed that when human umbilical vein endothelial cells (HUVECs) were treated with 3D-MVs, miR-210 was expressed at a higher level than in the control (CTRL), and that when neural stem cells (NSCs) were treated with 3D-MVs, miR-137 and miR-184 were expressed at higher levels than in the control (CTRL).

Figure 6E:
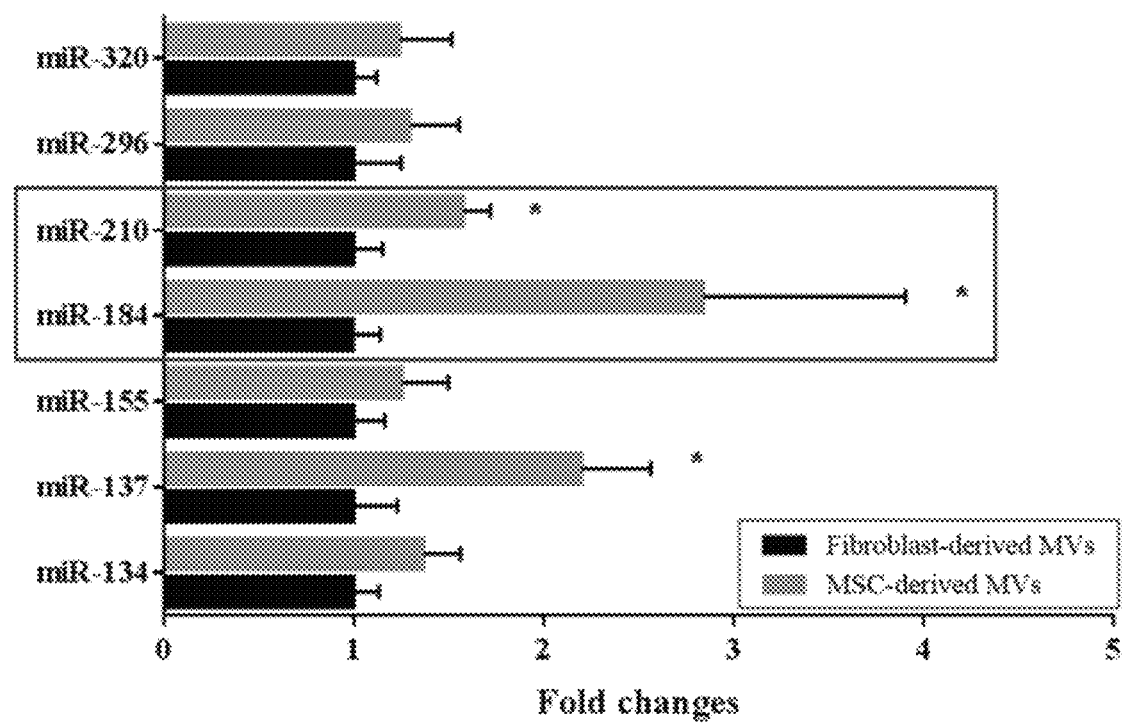
FIG. 6E is a result of measuring and comparing the expression levels of the microRNAs in ischemic brain extract-treated rMSC-derived microvesicles (MSC-MVs) and fibroblast-derived microvesicles (fibroblast-MVs)

Furthermore, as a result of comparing the contents of microRNAs of the ischemic brain extract-treated rMSC-derived microvesicles and the fibroblast-derived microvesicles, it could be seen that the expressions of miR-210, miR-184, and miR-137 were significantly increased in the rMSC-derived microvesicles (MSC-derived MVs), as illustrated in FIG. 6E, and through this, it could be seen that the expressions of the therapeutic microRNAs were specifically increased in MSCs by the treatment with the ischemic brain extract.

From the results, it was confirmed that various therapeutic cytokines and microRNAs associated with immunoregulation, neovascularization, and neurogenesis were abundantly present in the ischemic brain extract-treated MSC-derived microvesicles and dynamically 3D cultured MSC-derived microvesicles.

Example 5. Verification of Angiogenesis Effects and Neurogenesis Stimulation Effects of MSC-Derived Microvesicles 5-1. Confirmation of Ability of IBE-MV and 3D-MV to Produce Blood Vessels The present inventors investigated the therapeutic effect of microvesicles collected using an in vitro model for angiogenesis and neurogenesis. First, in order to evaluate the ability of each of the ischemic brain extract-treated hMSC-derived microvesicles (IBE-MVs) and the dynamically 3D cultured hMSC-derived microvesicles to produce blood vessels, human umbilical vein endothelial cells (HUVECs) inoculated on Matrigel were treated with 3 µg/mL of each of IBE-MVs and 3D-MVs, and the degrees of angiogenesis were compared through the loop numbers, branch numbers, and branch lengths produced with the control to which only a basic medium was added, or a vascular endothelial growth factor (VEGF)-treated group.

Figure 7A:
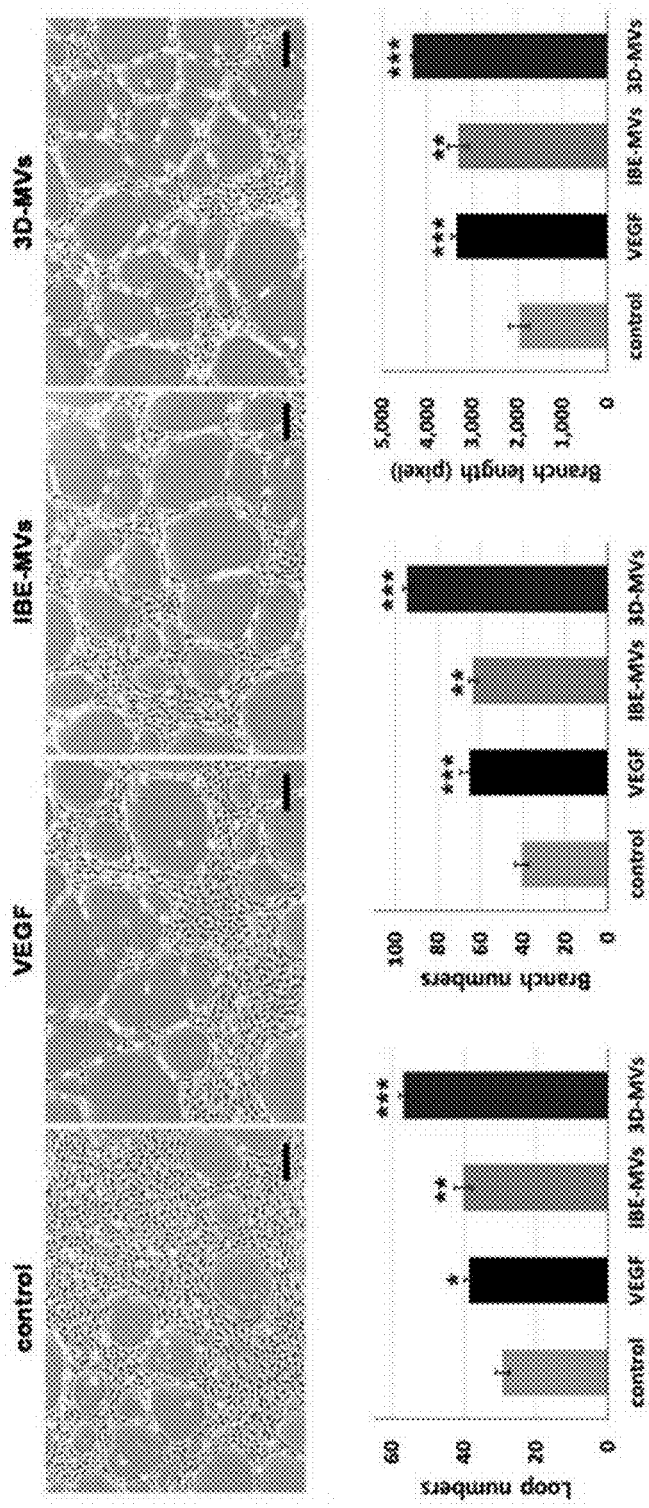
FIG. 7A is a result of treating human umbilical vein endothelial cells (HUVECs) with ischemic brain extract-treated MSC-derived microvesicles (IBE-MVs) and hMSC-derived microvesicles (3D-MVs) cultured by the dynamic 3D culture method and evaluating the degree of angiogenesis.

As a result, as illustrated in FIG. 7A, in the case of treatment with the VEGF, the degree of tube formation was significantly increased as compared to the control, and in the case of treatment with IBE-MVs, the tube formation was induced at a level similar to that of the VEGF-treated group. Further, it was confirmed that in the case of treatment with 3D-MVs, the tube formation was induced at a higher level.

In addition, the therapeutic effects of 3D-MVs and miR-210 collected using an in vitro model for angiogenesis were examined. First, in order to evaluate the ability of each of 3D-MVs and miR-210 to produce blood vessels, human umbilical vein endothelial cells (HUVECs) inoculated on Matrigel were transfected with non-specific miRNA and/or miR-210, and then treated with 3 µg/mL of each type of 3D-MV, and the degrees of angiogenesis were compared through the loop numbers, branch numbers, and branch lengths produced with the control to which only a basic medium was added, or a vascular endothelial growth factor (VEGF)-treated group.

Figure 7B:
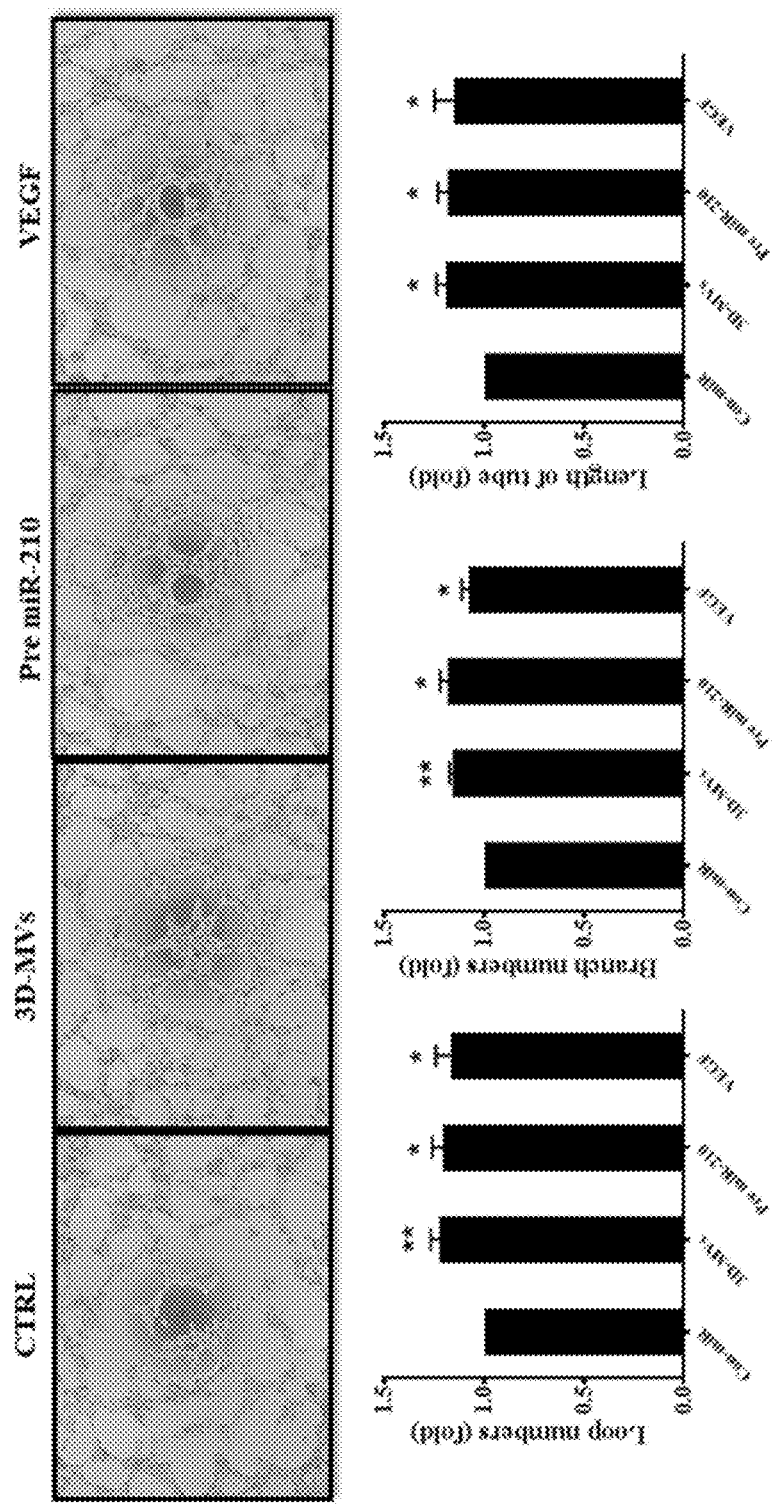
FIG. 7B is a result of evaluating the degree of angiogenesis of cells transfected with 3D-MVs and miR-210.

As a result, as illustrated in FIG. 7B, in the case of treatment with VEGF, the degree of tube formation was significantly increased as compared to the control, and in the case of treatment with 3D-MVs, the tube formation was induced at a level similar to that of the VEGF-treated group. In addition, it was confirmed that even when the cells were transfected with miR-210, the tube formation was induced at a high level.

Figure 7C:
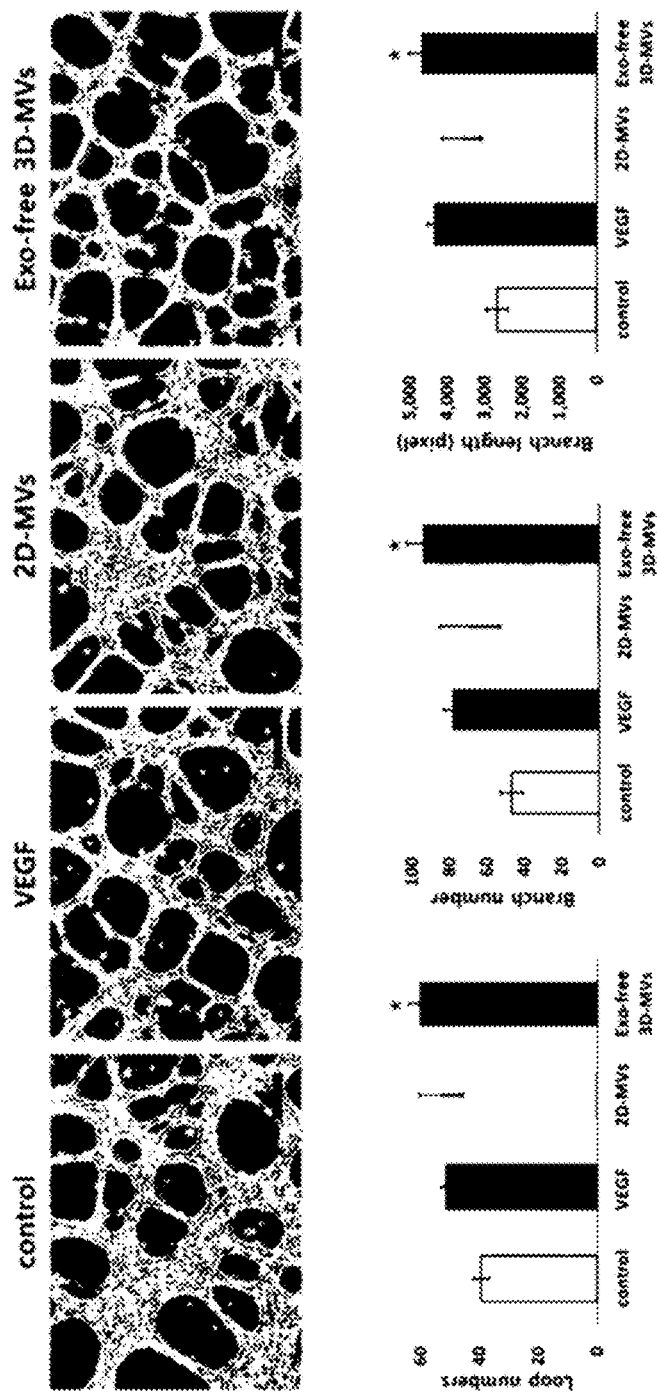
FIG. 7C is a result of evaluating the degree of angiogenesis after treatment with MSC-derived microvesicles cultured by the 2D culture method and the dynamic 3D culture method using the exosome-free FBS (2D-MVs and Exo-free 3D-MVs, respectively)

Furthermore, in order to verify the improvement of ability of MSC-derived microvesicles to produce blood vessels according to the dynamic 3D culture method, the HUVECs were treated in the same manner as in the aforementioned method using hMSC-derived microvesicles (2D-MVs and Exo-free 3D-MVs, respectively) cultured by the 2D culture method and the dynamic 3D culture method using exosome-free FBS, and then the results thereof were compared. As a result, as illustrated in FIG. 7C, it was confirmed that the treatment with Exo-free 3D-MVs induced angiogenesis at a significantly higher level compared to the treatment with 2D-MVs.

5-2. Confirmation of Ability of IBE-MV and 3D-MV to Stimulate Neurogenesis

Next, in order to investigate the ability of each of the ischemic brain extract-treated hMSC-derived microvesicles (IBE-MVs) and dynamically 3D cultured hMSC-derived microvesicles to stimulate neurogenesis, primary cultured neural stem cells (NSCs) from the cerebral cortex isolated from the embryo of a 14.5 day-old SD rat were treated with 3 µg/mL of each of the ischemic brain extract-treated hMSC-derived microvesicles (IBE-MVs) or the dynamically 3D cultured hMSC-derived microvesicles (3D-MV), and then the neurogenesis abilities were compared with the control to which only a basic medium was added or a nerve growth factor (NGF)-treated group.

Figure 8A:
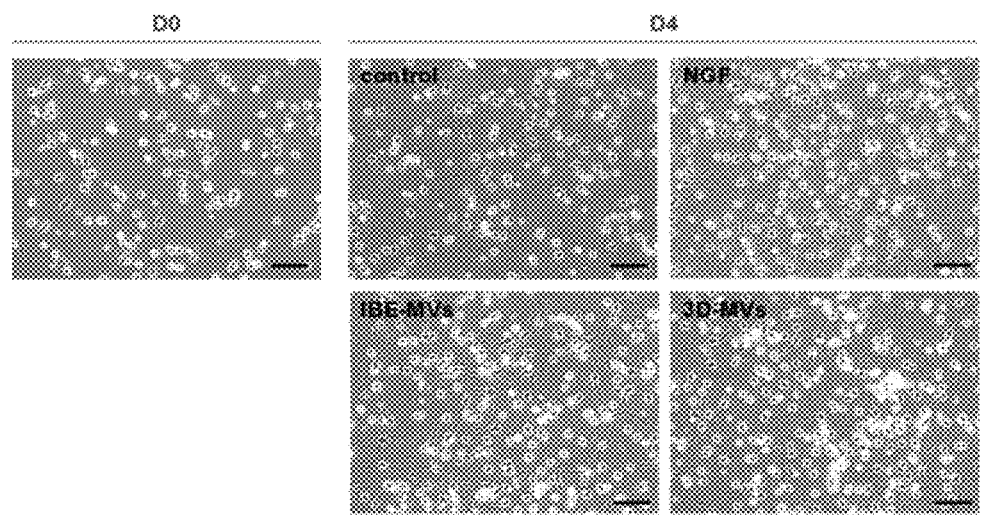
FIGS. 8A and 8B are results of treating rat-derived neural stem cells with ischemic brain extract-treated MSC-derived microvesicles (IBE-MVs) and hMSC-derived microvesicles cultured by the dynamic 3D culture method (3D-MVs), and evaluating the ability to stimulate neurogenesis through microscopic observation (FIG. 8A) and immunocytochemistry (FIG. 8B) on day 4 after the culture.
Figure 8B:
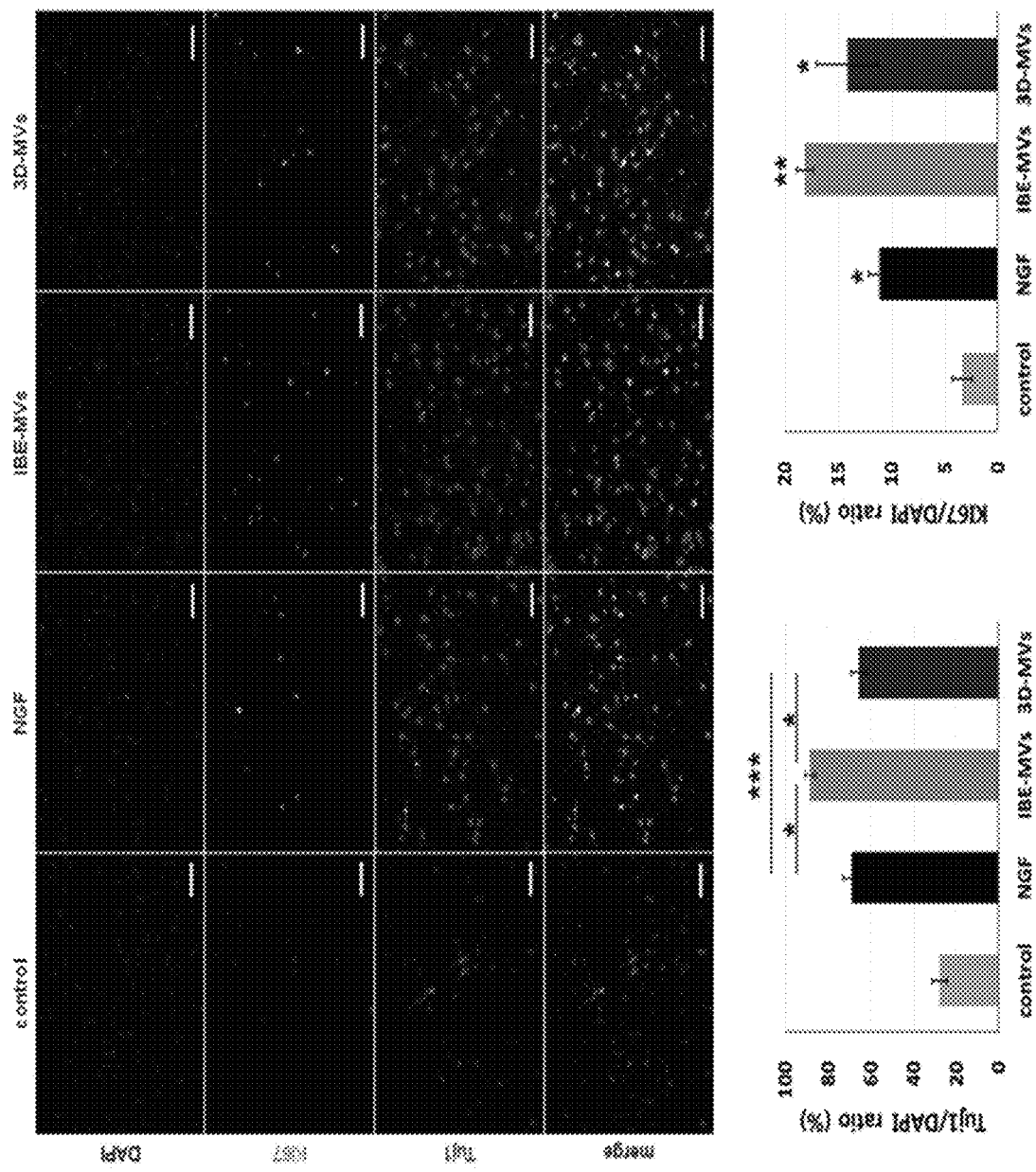

First, as illustrated in FIG. 8A, as a result of treating the microvesicles by the method and observing the microvesicles under a microscope on day 4 of the culture, it was found that the differentiation into nerve cells was induced in the NGF, IBE-MV, and 3D-MV treatment groups as compared to the control. Further, as illustrated in FIG. 8B, as a result of evaluating the degree of differentiation into the resulting neural cells by quantifying the expression of Tuj1 in the NSCs on day 4 through immunocytochemistry, and evaluating the proliferation rate of neural stem cells by quantifying the degree of expression of Ki67, it was confirmed that in the case of IBE-MV, the ability of neural stem cells to stimulate neurogenesis was shown to be the highest, and it was also confirmed that the 3D-MV induced neural differentiation and proliferation of NSCs, which are similar to those of the NGF-treated group.

Figure 8C:
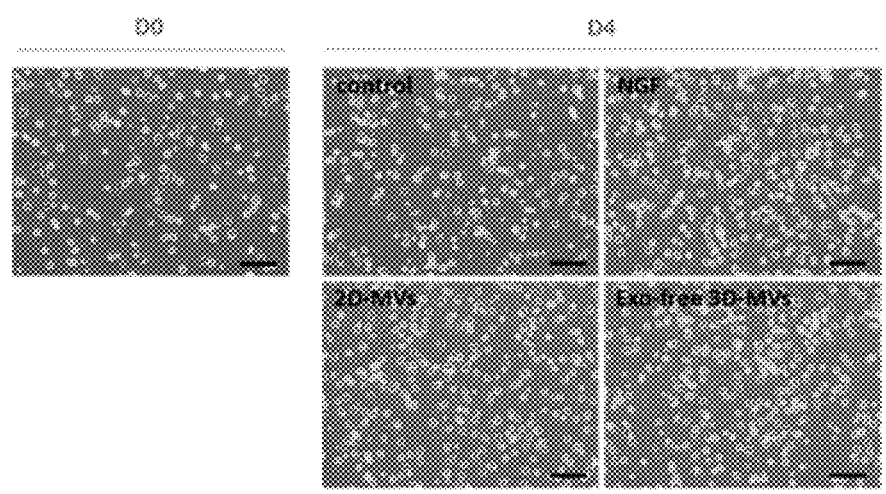
FIGS. 8C and 8D are results of evaluating the ability to stimulate neurogenesis through a microscopic observation (FIG. 8C) and immunocytochemistry (FIG. 8D) on day 4 of the culture after treatment with MSC-derived microvesicles cultured by the 2D culture method and the dynamic 3D culture method using exosome-free FBS (2D-MVs and Exo-free 3D-MVs, respectively)
Figure 8D:
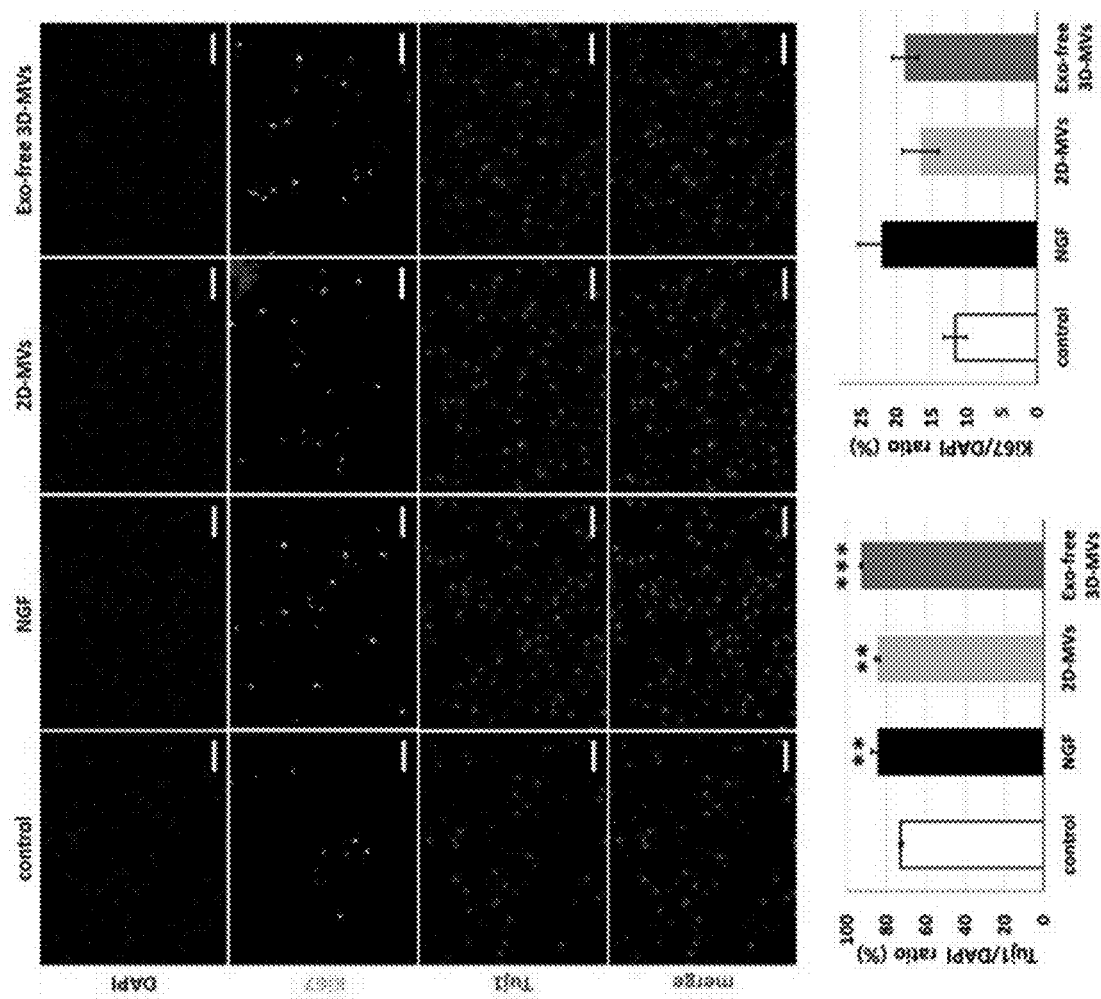

In addition to the results, in order to verify the ability of MSC-derived microvesicles to stimulate neurogenesis by the dynamic 3D culture method, the primary cultured neural stem cells (NSCs) were treated with 3 µg/mL each of hMSC-derived microvesicles (2D-MVs and Exo-free 3D-MVs, respectively) cultured by each of the 2D culture method and the dynamic 3D culture method using exosome-free FBS, and then a comparison was made with the control or the NGF-treated group. As a result, as a result of treating the microvesicles by the method and observing the microvesicles under a microscope on day 4 of the culture, as illustrated in FIG. 8C, it was found that differentiation into neural cells was induced in NGF, 2D-MV, and Exo-free 3D-MV treatment groups as compared to the control. In addition, as a result of performing immunocytochemical staining as illustrated in FIG. 8D, it was confirmed that a significant difference was not shown in the proliferation of neural cells through the expression of Ki67, whereas as a result of quantifying the expression of Tuj1, differentiation into neural cells was increased at a significant level in the NGF and 2D-MV treatment groups, and differentiation into neural cells was induced at a higher level in the Exo-free 3D-MV treatment group.

Furthermore, in order to evaluate the ability of each of 3D-MVs and miR-184 to proliferate neural stem cells, after neural stem cells (NSCs) were transfected with non-specific miRNA and/or miR-184, and then treated with 3 µg/mL of 3D-MV, the degrees of proliferation rate of neural stem cells were compared by quantifying the degree of expression of Ki67/DAPI with the control (CTRL) to which only a basic medium was added.

Figure 8E:
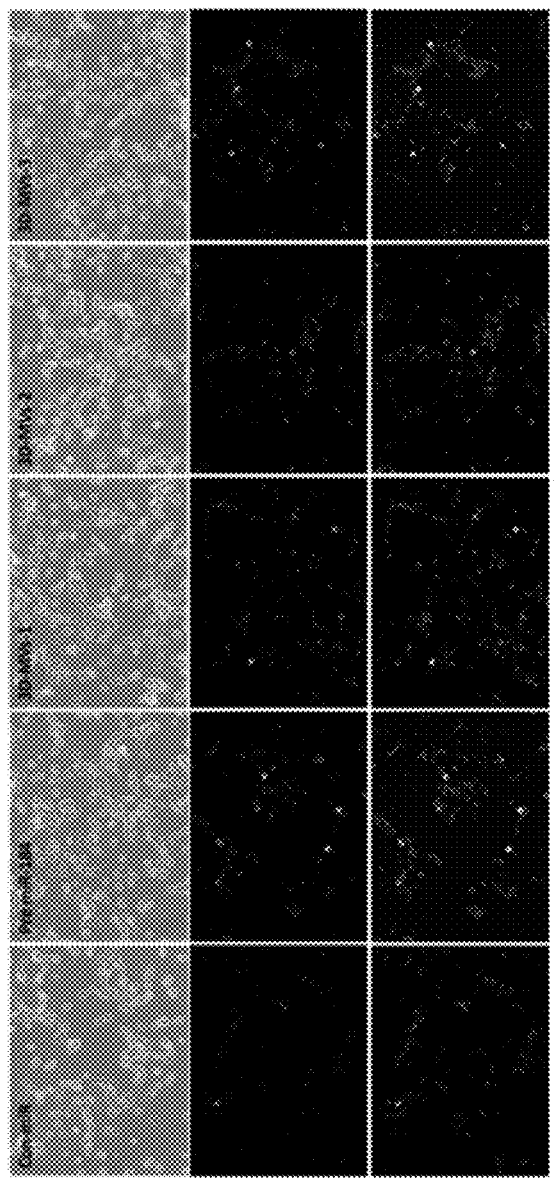
FIG. 8E is a result of evaluating the ability of cells transfected with 3D-MVs and miR-184 to proliferate neural stem cells.
Figure 8E:
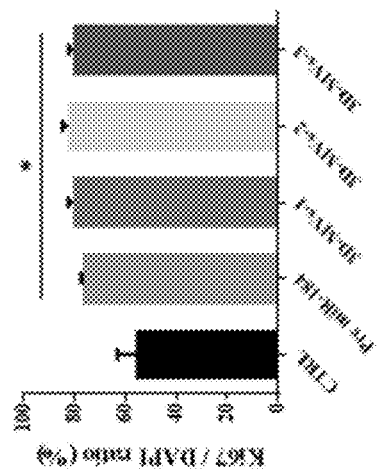

As a result, as illustrated in FIG. 8E, it was confirmed that the proliferation of neural stem cells was significantly increased in a group transfected with miR-184 or treated with 3D-MVs, as compared to the control.

From the results, it could be seen that the ability of stem cell-derived microvesicles to stimulate angiogenesis and neurogenesis was improved by the dynamic 3D culture method according to the present invention as compared to the 2D culture method.

5-3. Verification of Effects by Therapeutic microRNAs in IBE-MVs

Through the results of the examples, the present inventors confirmed that therapeutic microRNAs were contained at high levels in the ischemic brain extract-treated hMSC-derived microvesicles and the dynamically 3D cultured hMSC-derived microvesicles, and the ability to stimulate neovascularization and neurogenesis, and thus intended to verify whether the therapeutic microRNAs contained in the microvesicles affected the ability of the microvesicles as described above.

Figure 9A:
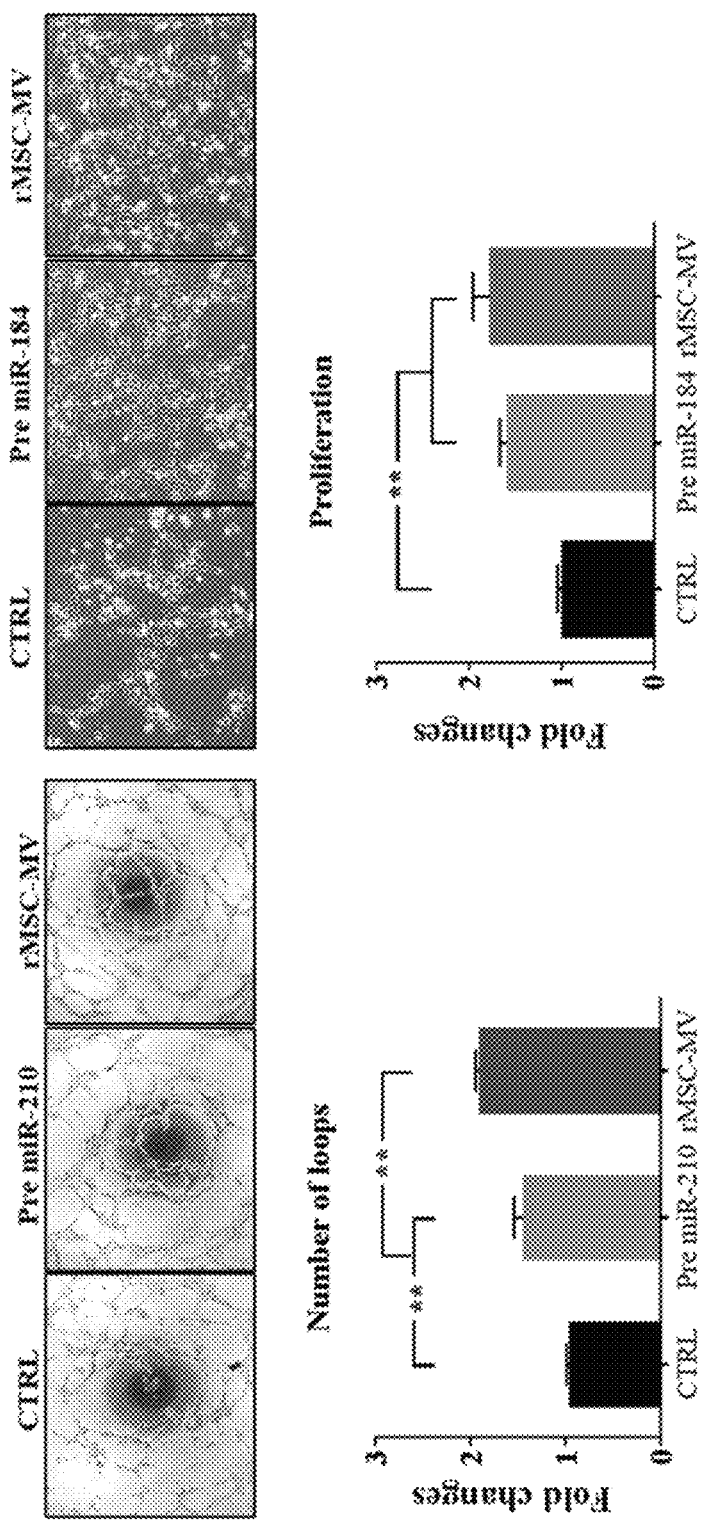
FIG. 9A is a result of evaluating the angiogenesis ability and the degree of neural stem cell proliferation by comparing ischemic brain extract-treated rMSC-derived microvesicles (rMSC-MVs) with the case where cells are transfected with microRNA-210 or microRNA-184.

For this purpose, first, HUVECs were transfected with miR-210 or treated with the ischemic brain extract-treated rMSC-derived microvesicles (rMSC-MVs), and the degrees of angiogenesis were compared, and a neural stem cell line (ReN cell) was transfected with miR-184 associated with neurogenesis, or treated with the ischemic brain extract-treated rMSC-derived microvesicles (rMSC-MVs), and cultured for 48 hours, and then the neurogenesis abilities were compared. As a result, as illustrated in FIG. 9A, it was shown that when HUVECs were transfected with miR-210, angiogenesis was significantly increased as compared to the negative control, and when HUVECs were treated with rMSC-MVs, angiogenesis was induced at a higher level than when HUVECs was transfected with miR-210, and it was also confirmed that when miR-184 was introduced, the proliferation of neural stem cells was significantly increased as compared to the negative control (CTRL) transfected with non-specific miRNA instead of miR-184, and even when the microvesicles were treated similarly, the proliferation of neural stem cells was increased.

Figure 9B:
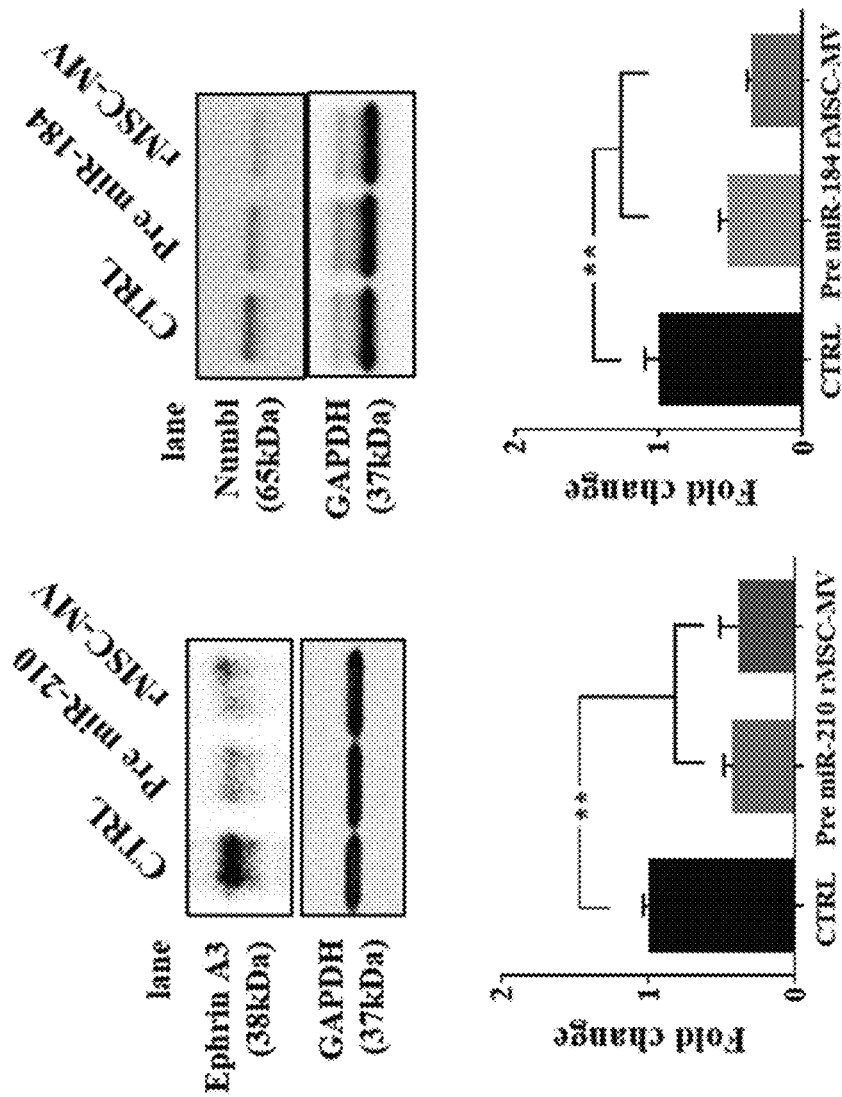
FIG. 9B is a result of confirming the inhibition of expression of Ephrin A3 and Numbl, which are target proteins of the microRNAs in cells treated with rMSC-MVs or cells transfected with miR-210 and miR-184, respectively, through western blot
Figure 9C:
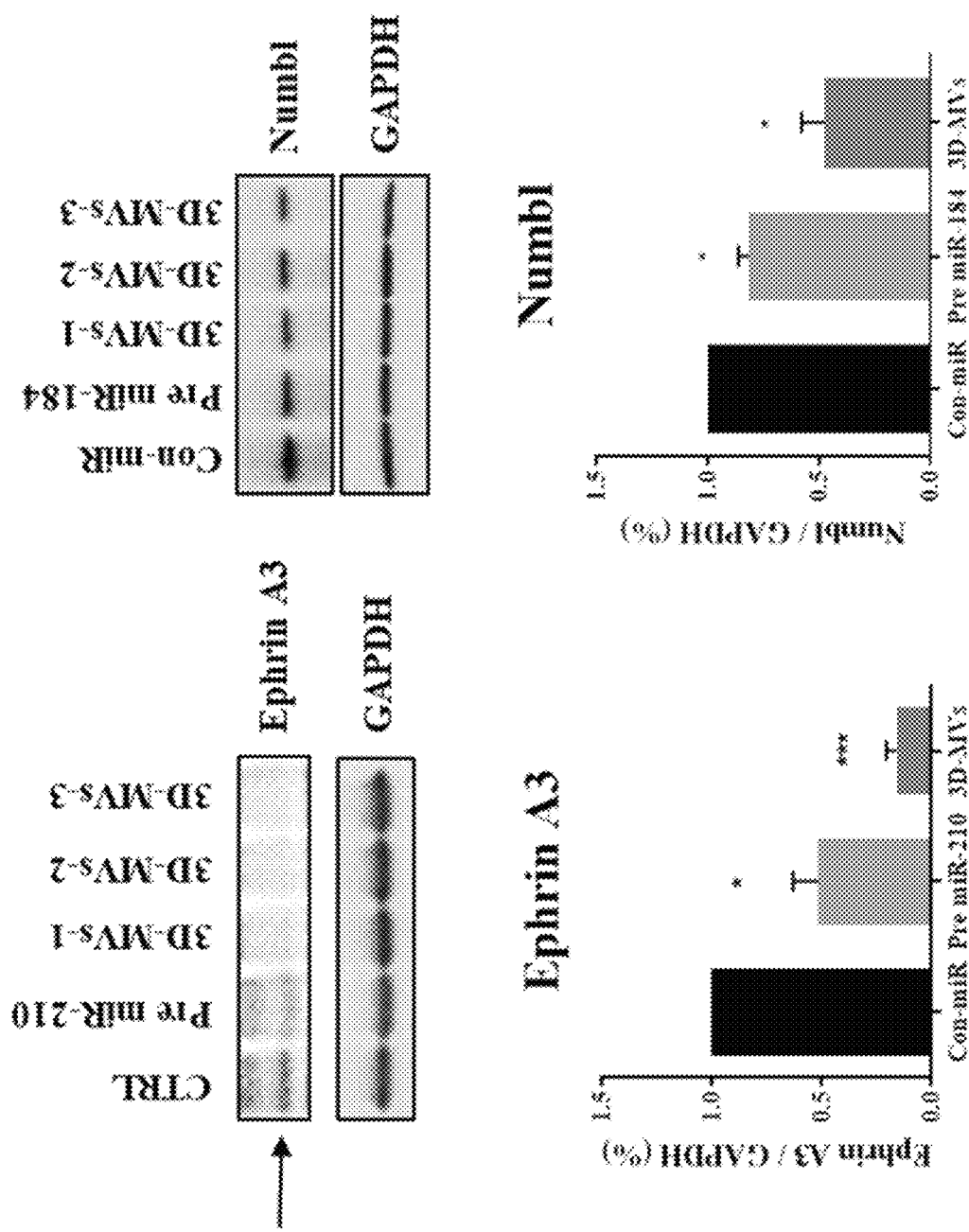
FIG. 9C is a result of confirming the inhibition of expression of Ephrin A3 and Numbl, which are target proteins of the microRNAs in cells treated with 3D-MVs or cells transfected with miR-210 and miR-184, respectively, through western blot.

In addition, western blotting was performed in order to analyze whether the microRNAs inhibited the expression of a target protein. More specifically, after the control and transfected cells were washed with a PBS buffer solution, the control and the transfected cells were lysed with a lysis buffer and proteins were separated by size by performing SDS-polyacrylamide gel electrophoresis (SDS-PAGE) using a predetermined amount of a lysate, and then transferred to a nitrocellulose membrane, and the expression levels of Ephrin A3 and Numbl, which are respective target proteins of miR-210 and miR-184, were observed. As a result, as illustrated in FIGS. 9B and 9C, it was confirmed that when HUVECs were transfected with miR-210 and miR-184, the expression levels of Ephrin A3 and Numbl were shown to be decreased, respectively, and the expression of Ephrin A3 and Numbl was remarkably inhibited in cells treated with rMSC-MVs or cells treated with 3D-MVs, respectively.

From the result, it could be seen that in cells treated with rMSC-MVs or cells treated with 3D-MVs, miR-210 and miR-184 contained in the microvesicles could mediate the stimulation of angiogenesis and neurogenesis by inhibiting the expression of Ephrin A3 and Numbl, respectively.

Since the method according to the present invention has excellent effects capable of promoting the production of stem cell-derived microvesicles and microRNAs in the microvesicles and capable of enhancing the efficacy of stem cells or microvesicles isolated therefrom, it is possible to obtain stem cell-derived microvesicles containing high levels of materials including therapeutic microRNAs efficiently and in large quantities through this, and thus, the microvesicles are expected to be able to be usefully used in related research fields and future clinical settings.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for promoting the production of microRNAs in mesenchymal stem cell-derived microvesicles, comprising a step of dynamic 3-dimensionally culturing mesenchymal stem cells with shaking by preparing a PEG hydrogel microwell array for spontaneous induction and formation of spheroids.

2. The method of claim 1, wherein the microRNA is miR-137, miR-184, or miR-210.

3. The method of claim 1, wherein the stem cell is an embryonic stem cell, an induced pluripotent stem cell (iPSC), or an adult stem cell.

4. The method of claim 3, wherein the adult stem cell is one or more adult stem cells selected from the group consisting of a mesenchymal stem cell, a human tissue-derived mesenchymal stromal cell, and a human tissue-derived mesenchymal stem cell.

5. The method of claim 1, wherein the 3-dimensional culture with shaking is culturing cells for 5 days to 9 days while performing rotation shaking in an incubator at 20 to 40 rpm 6 hours to 18 hours after seeding cells.

6. A method for enhancing the efficacy of mesenchymal stem cells or microvesicles isolated therefrom, comprising a step of dynamic 3-dimensionally culturing mesenchymal stem cells with shaking by preparing a PEG hydrogel microwell array for spontaneous induction and formation of spheroids, wherein the efficacy enhancement is an enhanced expression of a growth factor, a cytokine, or a microRNA in stem cells.

7. The method of claim 6, wherein the growth factor is one or more selected from the group consisting of a fibroblast growth factor (FGF), a hepatocyte growth factor (HGF), a vascular endothelial growth factor (VEGF), a transforming growth factor beta (TGFβ), and bone morphogenetic protein 2 (BMP2).

8. The method of claim 6, wherein the cytokine is one or more selected from the group consisting of CH13L1, CD105, CD147, ICAM-1, IP-10, MIP-1β, IL-6, IL-8, GRO, TIMP-1, and SerpineE1.

9. The method of claim 6, wherein the microRNA is miR-137, miR-184, or miR-210.

10. The method of claim 6, wherein the stem cell is an embryonic stem cell, an induced pluripotent stem cell (iPSC), or an adult stem cell.

11. The method of claim 10, wherein the adult stem cell is one or more adult stem cells selected from the group consisting of a mesenchymal stem cell, a human tissue-derived mesenchymal stromal cell, and a human tissue-derived mesenchymal stem cell.

* * * * *